(12) United States Patent
Drmanac et al.

(10) Patent No.: US 10,190,162 B2
(45) Date of Patent: Jan. 29, 2019

(54) SIGNAL CONFINEMENT SEQUENCING (SCS) AND NUCLEOTIDE ANALOGUES FOR SIGNAL CONFINEMENT SEQUENCING

(71) Applicant: Complete Genomics, Inc., Mountain View, CA (US)

(72) Inventors: Snezana Drmanac, Los Altos Hills, CA (US); Handong Li, San Jose, CA (US); Radoje Drmanac, Los Altos Hills, CA (US); Eric Harness, Sunnyvale, CA (US); Chongjun Xu, San Jose, CA (US)

(73) Assignee: Complete Genomics, Inc., San Jose, CA (US)

( * ) Notice: Subject to any disclaimer, the term of this patent is extended or adjusted under 35 U.S.C. 154(b) by 325 days.

(21) Appl. No.: 14/921,466

(22) Filed: Oct. 23, 2015

(65) Prior Publication Data
US 2016/0130647 A1   May 12, 2016

Related U.S. Application Data

(60) Provisional application No. 62/067,952, filed on Oct. 23, 2014.

(51) Int. Cl.
*C12Q 1/68* (2018.01)
*C12Q 1/6874* (2018.01)
*C07H 19/207* (2006.01)
*C07H 19/10* (2006.01)
*C07H 19/20* (2006.01)
*C12Q 1/6869* (2018.01)

(52) U.S. Cl.
CPC ........... *C12Q 1/6874* (2013.01); *C07H 19/10* (2013.01); *C07H 19/20* (2013.01); *C07H 19/207* (2013.01); *C12Q 1/6869* (2013.01)

(58) Field of Classification Search
CPC .................................................. C12Q 1/6874
USPC .......................... 435/6.1, 91.1; 536/4.1, 23.1
See application file for complete search history.

(56) References Cited

U.S. PATENT DOCUMENTS

| | | |
|---|---|---|
| 6,255,083 B1 | 7/2001 | Williams |
| 6,613,560 B1 | 9/2003 | Tso et al. |
| 6,750,018 B2 | 6/2004 | Kambara et al. |
| 7,033,764 B2 | 4/2006 | Korlach et al. |
| 7,057,026 B2 | 6/2006 | Barnes et al. |
| 7,078,499 B2 | 7/2006 | Odedra et al. |
| 7,414,116 B2 | 8/2008 | Milton et al. |
| 7,427,673 B2 | 9/2008 | Balasubramanian et al. |
| 7,541,444 B2 | 6/2009 | Milton et al. |
| 7,566,537 B2 | 7/2009 | Balasubramanian et al. |
| 7,575,865 B2 | 8/2009 | Leamon et al. |
| 7,592,435 B2 | 9/2009 | Milton et al. |
| 7,678,894 B2 | 3/2010 | Siddiqi |
| 7,771,973 B2 | 8/2010 | Milton et al. |
| 7,772,384 B2 | 8/2010 | Balasubramanian et al. |
| 7,785,796 B2 | 8/2010 | Balasubramanian et al. |
| 7,795,424 B2 | 9/2010 | Liu et al. |
| 7,816,503 B2 | 10/2010 | Milton et al. |
| 7,858,788 B2 | 12/2010 | Yoshida et al. |
| 8,071,739 B2 | 12/2011 | Milton et al. |
| 8,084,590 B2 | 12/2011 | Milton et al. |
| 8,148,064 B2 | 4/2012 | Balasubramanian et al. |
| 8,158,346 B2 | 4/2012 | Balasubramanian et al. |
| 8,178,360 B2 | 5/2012 | Barnes et al. |
| 8,212,015 B2 | 7/2012 | Milton et al. |
| 8,394,586 B2 | 3/2013 | Balasubramanian et al. |
| 8,481,259 B2 | 7/2013 | Gordon et al. |
| 8,513,298 B2 | 8/2013 | Canales et al. |
| 8,597,881 B2 | 12/2013 | Milton et al. |
| 8,612,161 B2 | 12/2013 | Gordon et al. |
| 8,623,598 B2 | 1/2014 | Olejnik et al. |
| 8,754,244 B1 | 6/2014 | Romanov et al. |
| 8,809,551 B1 | 8/2014 | Romanov et al. |
| 8,883,999 B2 | 11/2014 | Olejnik et al. |
| 8,884,030 B2 | 11/2014 | Canales et al. |
| 8,900,810 B2 | 12/2014 | Gordon et al. |
| 9,035,081 B2 | 5/2015 | Gao et al. |
| 2003/0104437 A1 | 6/2003 | Barnes et al. |
| 2003/0194722 A1 | 10/2003 | Odedra et al. |
| 2004/0096853 A1 | 5/2004 | Mayer |
| 2004/0152119 A1* | 8/2004 | Sood .................... C12Q 1/6858 435/6.12 |
| 2006/0160081 A1 | 7/2006 | Milton et al. |
| 2007/0042407 A1 | 2/2007 | Milton et al. |
| 2007/0048773 A1 | 3/2007 | Lee et al. |
| 2007/0109536 A1 | 5/2007 | Weiss et al. |

(Continued)

FOREIGN PATENT DOCUMENTS

| | | |
|---|---|---|
| CN | 103866010 | 6/2014 |
| DE | 202013010956 | 12/2014 |

(Continued)

OTHER PUBLICATIONS

Grimm et al., The Chemistry of Small-Molecule Fluorogenic Probes, Progress in Molecular Biology and Translational Science, vol. 113, 2013, pp. 1-34.
Oushiki et al., Near-Infrared Fluorescence Probes for Enzymes Based on Binding Affinity Modulation of Squarylium Dye Scaffold, Analytical Chemistry, vol. 84, Issue 10, 2012, pp. 4404-4410.
Sims et al., Fluorogenic DNA Sequencing in PDMS Microreactors, Nature Methods, vol. 8, Issue 7, 2011, pp. 575-580.
International Application No. PCT/US2015/057094, International Search Report and Written Opinion dated Feb. 16, 2016, 10 pages.

*Primary Examiner* — Jezia Riley
(74) *Attorney, Agent, or Firm* — Kilpatrick Townsend and Stockton LLP

(57) ABSTRACT

Novel fluorescent nucleotide analogs are provided herein. Also provided herein are methods of using the nucleotide analogs in sequencing-by-synthesis and signal confinement methods.

20 Claims, 13 Drawing Sheets

Specification includes a Sequence Listing.

(56) References Cited

U.S. PATENT DOCUMENTS

| | | |
|---|---|---|
| 2007/0166705 A1 | 7/2007 | Milton et al. |
| 2008/0161271 A1 | 7/2008 | Yoshida et al. |
| 2009/0062145 A1 | 3/2009 | Liu et al. |
| 2009/0325172 A1 | 12/2009 | Milton et al. |
| 2010/0009353 A1 | 1/2010 | Barnes et al. |
| 2010/0035252 A1 | 2/2010 | Rothberg et al. |
| 2010/0035253 A1 | 2/2010 | Gordon et al. |
| 2010/0063743 A1 | 3/2010 | Gordon et al. |
| 2010/0068722 A1 | 3/2010 | Milton et al. |
| 2010/0159531 A1 | 6/2010 | Gordon et al. |
| 2010/0292452 A1 | 11/2010 | Milton et al. |
| 2010/0311178 A1 | 12/2010 | Liu et al. |
| 2010/0323350 A1 | 12/2010 | Gordon et al. |
| 2011/0014611 A1 | 1/2011 | Ju et al. |
| 2011/0020827 A1 | 1/2011 | Milton et al. |
| 2011/0039259 A1 | 2/2011 | Ju et al. |
| 2011/0124054 A1 | 5/2011 | Olejnik et al. |
| 2011/0178129 A1 | 7/2011 | Canales et al. |
| 2012/0052489 A1 | 3/2012 | Gordon et al. |
| 2012/0095201 A1 | 4/2012 | Milton et al. |
| 2012/0156671 A1 | 6/2012 | Liu et al. |
| 2013/0053252 A1 | 2/2013 | Xie et al. |
| 2013/0079232 A1 | 3/2013 | Kain et al. |
| 2013/0137091 A1 | 5/2013 | Gordon et al. |
| 2013/0189743 A1 | 7/2013 | Balasubramanian et al. |
| 2013/0197209 A1 | 8/2013 | Milton et al. |
| 2013/0264207 A1 | 10/2013 | Ju et al. |
| 2013/0301888 A1 | 11/2013 | Gordon et al. |
| 2013/0315861 A1 | 11/2013 | Canales et al. |
| 2013/0316914 A1 | 11/2013 | Gordon et al. |
| 2013/0323203 A1 | 12/2013 | Canales et al. |
| 2014/0001055 A1 | 1/2014 | Elibol et al. |
| 2014/0093869 A1 | 4/2014 | Ju et al. |
| 2014/0113282 A1 | 4/2014 | Balasubramanian et al. |
| 2014/0141414 A1 | 5/2014 | Liu et al. |
| 2014/0234832 A1 | 8/2014 | Olejnik et al. |
| 2014/0255917 A1 | 9/2014 | Romanov et al. |
| 2014/0255920 A1 | 9/2014 | Romanov et al. |
| 2014/0322713 A1 | 10/2014 | Romanov et al. |
| 2015/0031920 A1 | 1/2015 | Katayama et al. |
| 2015/0038339 A1 | 2/2015 | Gordon et al. |

FOREIGN PATENT DOCUMENTS

| | | |
|---|---|---|
| EP | 2830125 | 1/2015 |
| FR | 3008709 | 1/2015 |
| GB | 2471044 | 12/2010 |
| GB | 2516303 | 1/2015 |
| JP | 2015023123 | 2/2015 |
| RU | 2540089 | 1/2015 |
| WO | 9309096 | 5/1993 |
| WO | 9509175 | 4/1995 |
| WO | 0192284 | 12/2001 |
| WO | 2004018493 | 3/2004 |
| WO | 2004018497 | 3/2004 |
| WO | 2007042407 | 4/2007 |
| WO | 2007135368 | 11/2007 |
| WO | 2009051807 | 4/2009 |
| WO | 2009054922 | 4/2009 |
| WO | 2009100382 | 8/2009 |
| WO | 2009114182 | 9/2009 |
| WO | 2009117119 | 9/2009 |
| WO | 2010117420 | 10/2010 |
| WO | 2012027625 | 3/2012 |
| WO | 2012083249 | 6/2012 |
| WO | 2012162429 | 11/2012 |
| WO | 2013044018 | 3/2013 |
| WO | 2013154999 | 10/2013 |
| WO | 2014135221 | 9/2014 |
| WO | 2014135223 | 9/2014 |
| WO | 2014139596 | 9/2014 |
| WO | 2014144883 | 9/2014 |
| WO | 2014158943 | 10/2014 |
| WO | 2015013715 | 1/2015 |
| WO | 2016065248 | 4/2016 |

* cited by examiner

DNB on
Silicon

DNB on
Silicon Surface

SEQUENCE LISTING

```
<160> NUMBER OF SEQ ID NOS: 1

<210> SEQ ID NO 1
<211> LENGTH: 14
<212> TYPE: DNA
<213> ORGANISM: Artificial Sequence
<220> FEATURE:
<223> OTHER INFORMATION: synthethic primer

<400> SEQUENCE: 1
gacttagtct gata                                                            14
```

SIGNAL CONFINEMENT SEQUENCING (SCS) AND NUCLEOTIDE ANALOGUES FOR SIGNAL CONFINEMENT SEQUENCING

REFERENCE TO RELATED APPLICATION

This application claims the priority benefit of U.S. provisional application 62/067,952, filed Oct. 23, 2014. The priority application is hereby incorporated herein in its entirety for all purposes.

FIELD

Disclosed herein are nucleotide analogues, methods for using the nucleotide analogues in sequencing-by-synthesis (SBS), and signal confinement methods.

BACKGROUND

Some methods for sequencing DNA and RNA suffer from inaccuracies in base addition, the introduction of scars to the DNA template, and unacceptably high background noise due to the presence of a dye in the reaction that impairs the dye signal. Efficient methods for sequencing DNA and RNA are needed.

SUMMARY

Described herein are nucleotide analogues of the following formula:

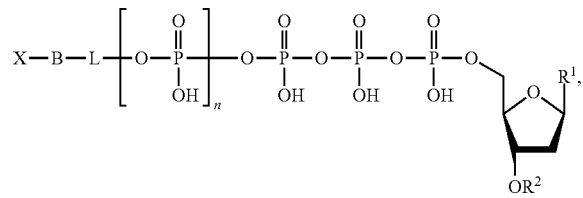

wherein n is 0, 1, 2, 3, 4, 5, 6, or 7; L is absent or a linking group; $R^1$ is a nucleoside base; $R^2$ is hydrogen or a blocking group; B is a binding molecule; and X is a detection label. In some embodiments, $R^2$ is a blocking group and the blocking group is $-NH_2$, $-CH_2CH=CH_2$, $-CH_2N_3$, polyethylene glycol, or a substituted or unsubstituted alkyl. In some embodiments, L is a linking group and the linking group is a substituted or unsubstituted alkyl, substituted or unsubstituted alkenyl, or substituted or unsubstituted aryl. Optionally, the linking group is a methylene group or a substituted phenyl group. The linking group can further include a quencher. Optionally, the binding molecule is biotin, an antibody, an amino acid, cholesterol, fluorescein isothiocyanate, or a peptide. Optionally, the detection label is a molecule containing a cationic group, a molecule containing an anionic group, a fluorescent molecule (e.g., a fluorescent dye), a fluorogenic molecule, a metal, a reduction tag, a thio containing molecule, or a substituted or unsubstituted alkyl.

Also described herein are methods for sequencing a target nucleic acid and for confining a signal. The methods for sequencing a target nucleic acid include providing a template nucleic acid, a primer, a polymerase, and a nucleotide analogue of the following structure:

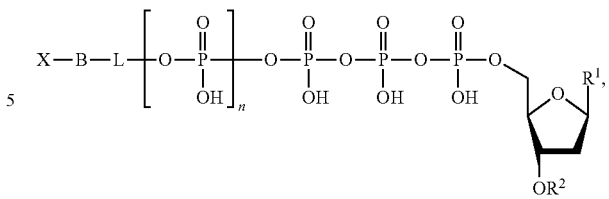

wherein n is 0, 1, 2, 3, 4, 5, 6, or 7; L is absent or a linking group; $R^1$ is a nucleoside base; $R^2$ is hydrogen or a blocking group; B is a binding molecule; and X is a detection label, wherein said detection label is quenched. The method further includes extending the primer by incorporating the nucleotide analogue; providing a phosphatase to cleave between the binding molecule and the linking group or between the binding molecule and the terminal phosphate, thereby generating a fragment of the nucleotide analogue comprising the label and the binding molecule, wherein the label is unquenched; binding the fragment to a capture element immobilized on a surface; and detecting a fluorescence emission from the label of the fragment captured on the surface. In some embodiments, the binding molecule comprises an oligonucleotide.

In some embodiments, the capture element is a thio or thiol containing molecule. In some embodiments, the capture element is streptavidin, an antibody, a protein, or a dendrimer. In some embodiments, the capture element comprises an oligonucleotide immobilized complementary to the template nucleic acid.

In some embodiments, the template nucleic acid is an immobilized DNA concatemer comprising multiple copies of a complementary capture sequence.

In some embodiments, the linking group further comprises a quencher. Optionally, the providing step can comprise displacing the quencher from the linking group.

In some embodiments, the method can further include removing the fragment from the capture element on the solid surface. Optionally, the removing step comprises heating the fragment and the capture element. Optionally, the removing step comprises washing the fragment and the capture element with a buffer. Optionally, the removing step comprises adding an enzyme to cleave the fragment from the capture element.

The method can further include cleaving the blocking group from the incorporated nucleotide analogue.

In some embodiments, the detecting step is performed using fluorescence resonance energy transfer.

Further described herein is a sequencing method. The sequencing method comprises combining a template nucleic acid, a primer complementary to the template, a nucleotide analogue comprising a nitrogenous base and a detectable label, and a polymerase; maintaining the components in the combining step under conditions in which the primer is extended in a primer extension reaction to produce a complementary polynucleotide, wherein the nitrogenous base is incorporated by the polymerase into the complementary polynucleotide and the detectable label is separated by the polymerase from the nitrogenous base and not incorporated into the complementary polynucleotide, and wherein the separated detectable label is bound by a capture element; and detecting the detectable label bound by the capture element, wherein said detecting provides sequence information.

The details of one or more embodiments are set forth in the drawings and the description below. Other features, objects, and advantages will be apparent from the description and drawings, and from the claims.

DEFINITIONS

Figure 1A:
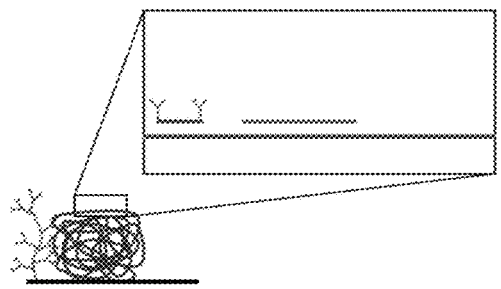
FIGS. 1A-D show steps of a sequencing-by-synthesis method using nucleotide analogues.

The term "detectable label," or "detection label," as used herein, refers to any atom or molecule that can be used to provide a detectable and/or quantifiable signal. Suitable labels include radioisotopes, fluorophores, chromophores, mass labels, electron dense particles, magnetic particles, spin labels, molecules that emit chemiluminescence, electrochemically active molecules, enzymes, cofactors, and enzyme substrates. In some embodiments, the detection label is a molecule containing a charged group (e.g., a molecule containing a cationic group or a molecule containing an anionic group), a fluorescent molecule (e.g., a fluorescent dye), a fluorogenic molecule, or a metal. Optionally, the detection label is a fluorogenic label. A fluorogenic label can be any label that is capable of emitting light when in an unquenched form (e.g., when not quenched by another agent). The fluorescent moiety emits light energy (i.e., fluoresces) at a specific emission wavelength when excited by an appropriate excitation wavelength. When the fluorescent moiety and a quencher moiety are in close proximity, light energy emitted by the fluorescent moiety is absorbed by the quencher moiety. Optionally, the detection label is a fluorogenic dye. In some embodiments, the fluorogenic dye is a fluorescein, a rhodamine, a phenoxazine, an acridine, a coumarin, or a derivative thereof. In some embodiments, the fluorogenic dye is a carboxyfluorescein. Further examples of suitable fluorogenic dyes include the fluorogenic dyes commercially available under the ALEXA FLUOR product line (Life Technologies; Carlsbad, Calif.). Optionally, the label is a redoxgenic label. Optionally, the label is a reduction tag, a thio-containing molecule, or a substituted or unsubstituted alkyl.

The term "dye" has its standard meaning in the art. The term "fluorescent dye," as used herein, generally refers to any dye that emits electromagnetic radiation of longer wavelength by a fluorescent mechanism upon irradiation by a source of electromagnetic radiation, such as a lamp, a photodiode, or a laser.

The term "reporter molecule" refers to a molecule capable of generating a fluorescence signal. A reporter molecule is an example of a detectable label. A "quencher molecule" refers to a molecule capable of absorbing the fluorescence energy of an excited reporter molecule, thereby quenching the fluorescence signal that would otherwise be released from the excited reporter molecule. In order for a quencher molecule to quench an excited fluorophore, it is often advantageous that the quencher molecule is within a minimum quenching distance of the excited reporter molecule at some time starting from the excitation of the reporter molecule, but prior to the reporter molecule releasing the stored fluorescence energy. In proximity based quenching applications, the reporter and quencher molecules are positioned sufficiently close to each other such that whenever the reporter molecule is excited, the energy of the excited state transfers to the quencher molecule where it either dissipates nonradiatively or is emitted at a different emission frequency than that of the reporter molecule. Several non-radiative energy transfer mechanisms work over shorter distances and are appropriate for proximity based quenching applications.

The terms "ligand" and "antiligand" refer to members of an antiligand pair. An "antiligand pair" refers to first and second molecules that specifically bind to each other. In general, "specific binding" of the first member of the binding pair to the second member of the binding pair in a sample is evidenced by the binding of the first member to the second member, or vice versa, with greater affinity and specificity than to other components in the sample. The binding between the members of the binding pair may be noncovalent. Binding partners need not be limited to pairs of single molecules. For example, a single ligand can be bound by the coordinated action of two or more antiligands. Binding between binding pairs or binding partners results in the formation of a binding complex, sometimes referred to as a ligand/antiligand complex or simply as ligand/antiligand. Exemplary binding pairs include, but are not limited to: (a) a haptenic or antigenic compound in combination with a corresponding antibody, or binding portion or fragment thereof; (b) a nucleic acid aptamer and protein; (c) nonimmunological binding pairs (e.g., biotin-avidin, biotin-streptavidin, biotin-Neutravidin); (d) hormone-hormone binding protein; (e) receptor-receptor agonist or antagonist; (f) lectin-carbohydrate; (g) enzyme-enzyme cofactor; (h)

enzyme-enzyme inhibitor; and (i) complementary oligonucleotide or polynucleotide pairs capable of forming nucleic acid duplexes.

DETAILED DESCRIPTION OF THE INVENTION

1. Overview

In one aspect, the invention provides improved systems for sequencing, e.g., sequencing-by-synthesis (SBS). These systems make use of nucleotide analogues that comprise a nitrogenous base (e.g., A, T, G or C) or analogue, which is incorporated into the newly synthesized template-complementary strand, and a releasable labeled moiety, called the tag element, which is separated from the base as a consequence of the incorporation. The systems also use a capture element that binds the tag element when it is released. The capture element is colocalized with the template nucleic acid so that the bound tag element can be associated with the template. The invention provides nucleotide analogues, methods of sequencing using the nucleotide analogues of the invention, and sequencing systems. These analogues, methods, and systems are described generally in this Section 1. Section 2 describes certain phosphatase cleavable nucleotide analogues that are particularly suited for use in the sequencing methods. Section 3 describes systems of the invention. Section 4 provides illustrative examples.

1.1 Nucleotide Analogs

In one aspect, nucleotide analogues of the invention comprise the Formula [I]:

[X—B]-[Q-K]-pN          [I]

In Formula [I], pN is a nucleotide or deoxyribonucleotide monophosphate, or analogues of either, comprising a nitrogenous base capable of base pairing with complementary nucleotides of a template nucleic acid. Typically, the nitrogenous base is selected from adenine (A), cytosine (C), guanine (G), thymine (T), uracil (U), and derivatives of these. K is a cleavable linking moiety comprising at least three (e.g., 3-10) phosphates, or analogues thereof, such that the nucleotide analogue is a substrate for a DNA polymerase. Q is a quenching moiety. In some embodiments [Q-K] is oligophosphate, and is both a cleavable linking moiety (e.g., substrate for alkaline phosphatase) and quenching moiety. X is a detectable label; B, referred to as the binding molecule, is a member of a ligand-antiligand pair. The tag element, referred to below, comprises [X—B]. The brackets surrounding X and B ([X—B]) indicate that X and B can be linked in any of a variety of structures, provided that cleavage at K separates X and B from Q, and does not separate X from B.

The detectable label X and quenching moiety Q interact, under detection conditions such as illumination, when they are in proximity to each other, such that the detectable signal (or absence of signal) of the label X in proximity to Q can be distinguished from the signal when X and Q are not in proximity, for example when cleavage at K destroys Q or allows X to diffuse away from Q such that they are physically separated. Examples of quencher-detectable label combinations are described below. One example of a quencher is an oligo-phosphate, as exemplified by US Pat Pub. 20130053252, incorporated herein by reference for all purposes.

In some embodiments, the detectable label is a reporter molecule capable of generating a fluorescence signal. Exemplary reporter molecules are fluorescent organic dyes, which may be derivatized for attachment to a nucleic acid or other organic molecule. Preferably, quencher molecules are also organic dyes, which may or may not be fluorescent, depending on the embodiment of the invention. For example, in a preferred embodiment of the invention, the quencher molecule is fluorescent. Generally, whether the quencher molecule is fluorescent or simply releases the transferred energy from the reporter by non-radiative decay, the absorption band of the quencher should substantially overlap the fluorescent emission band of the reporter molecule. Non-fluorescent quencher molecules (NFQMs), such as Black Hole quenchers, that absorb energy from excited reporter molecules, but which do not release the energy radiatively, are known in the art and may be used.

There is a great deal of practical guidance available in the literature for selecting appropriate reporter-quencher pairs for particular probes, as exemplified by the following references: Grimm et al., 2013, "The chemistry of small-molecule fluorogenic probes," Prog Mol Biol Transl Sci. 113:1-34, incorporated herein by reference, and Oushiki et al., 2012, "Near-infrared fluorescence probes for enzymes based on binding affinity modulation of squarylium dye scaffold," Anal Chem. 84:4404-10; Clegg, 1992, "Fluorescence resonance energy transfer and nucleic acids," *Methods of Enzymology*, 211:353-89; Wu et al. 1994, "Resonance energy transfer: methods and applications," *Anal. Biochem.* 218: 1-13; Pesce et al., editors, Fluorescence Spectroscopy (Marcel Dekker, New York, 1971); White et al., Fluorescence Analysis: A Practical Approach (Marcel Dekker, New York, 1970); and the like. The literature also includes references providing exhaustive lists of fluorescent molecules and NFQMs, and their relevant optical properties for choosing reporter-quencher pairs, e.g., Berlman, Handbook of Fluorescence Spectra of Aromatic Molecules, 2nd Edition (Academic Press, New York, 1971); Griffiths, Colour and Constitution of Organic Molecules (Academic Press, New York, 1976); Bishop, editor, Indicators (Pergamon Press, Oxford, 1972); Haugland, Handbook of Fluorescent Probes and Research Chemicals (Molecular Probes, Eugene, 1992) Pringsheim, Fluorescence and Phosphorescence (Interscience Publishers, New York, 1949); and the like. Further, there is extensive guidance in the literature for derivatizing reporter and quencher molecules for covalent attachment via common reactive groups that can be added to an oligonucleotide, as exemplified by the following references: Ullman et al., U.S. Pat. No. 3,996,345; Khanna et al., U.S. Pat. No. 4,351,760; and the like. Each of the aforementioned publications is incorporated herein by reference in its entirety for all purposes.

Exemplary reporter-quencher pairs may be selected from xanthene dyes, including fluoresceins, and rhodamine dyes. Many suitable forms of these compounds are widely available commercially with substituents on their phenyl moieties which can be used as the site for bonding or as the bonding functionality for attachment to an oligonucleotide. Another group of fluorescent compounds are the naphthylamines, having an amino group in the alpha or beta position. Included among such naphthylamino compounds are 1-dimethylaminonaphthyl-5-sulfonate, 1-anilino-8-naphthalene sulfonate, and 2-p-toluidinyl-6-naphthalene sulfonate. Other dyes include 3-phenyl-7-isocyanatocoumarin; acridines, such as 9-isothiocyanatoacridine and acridine orange; N-(p-(2-benzoxazolyl)phenyl)maleimide; benzoxadiazoles; stilbenes; pyrenes; and the like.

In some embodiments, reporter and quencher molecules are selected from fluorescein and rhodamine dyes. These dyes and appropriate linking methodologies are described in many references, e.g., Khanna et al. (cited above); Marshall, Histochemical J., 7:299-303 (1975); Menchen et al., U.S. Pat. No. 5,188,934; Menchen et al., European Patent Application 87310256.0; and Bergot et al., International Application PCT/US90/05565. Fluorophores that can be used as detectable labels for probes include, but are not limited to, rhodamine, cyanine 3 (Cy 3), cyanine 5 (Cy 5), fluorescein, Vic™, Liz™, Tamra™, 5-Fam™, 6-Fam™, 6-HEX, CAL Fluor Green 520, CAL Fluor Gold 540, CAL Fluor Orange 560, CAL Fluor Red 590, CAL Fluor Red 610, CAL Fluor Red 615, CAL Fluor Red 635, and Texas Red (Molecular Probes). In particular embodiments, molecules useful as quenchers include, but are not limited to, tetramethylrhodamine (TAMRA), DABCYL (DABSYL, DABMI or methyl red) anthroquinone, nitrothiazole, nitroimidazole, malachite green, Black Hole Quenchers™, e.g., BHQ1 (Biosearch Technologies), Iowa Black™ or ZEN quenchers (from Integrated DNA Technologies, Inc.), TIDE Quencher 2 (TQ2) and TIDE Quencher 3 (TQ3) (from AAT Bioquest).

The quencher can be dimethylaminozobenzenesulfonic acid; a BLACK HOLE QUENCHER dye, commercially available from Biosearch Technologies (Petaluma, Calif.); QXL Quenchers, commercially available from AnaSpec, Inc. (Fremont, Calif.); quenchers commercially available from Integrated DNA Technologies (Coralville, Iowa) under the IOWA BLACK product line, including IOWA BLACK FQ and IOWA BLACK RQ; and IRDYE QC-1, commercially available from LI-COR Biosciences (Lincoln, Nebr.).

By judicious choice of labels, analyses can be conducted in which the different labels are excited and/or detected at different wavelengths in a single reaction. See, e.g., Fluorescence Spectroscopy (Pesce et al., Eds.) Marcel Dekker, New York, (1971); White et al., Fluorescence Analysis: A Practical Approach, Marcel Dekker, New York, (1970); Berlman, Handbook of Fluorescence Spectra of Aromatic Molecules, 2nd ed., Academic Press, New York, (1971); Griffiths, Colour and Constitution of Organic Molecules, Academic Press, New York, (1976); Indicators (Bishop, Ed.). Pergamon Press, Oxford, 19723; and Haugland, Handbook of Fluorescent Probes and Research Chemicals, Molecular Probes, Eugene (1992). Typically, the distance between the reporter and quencher molecules will be minimized to increase the effectiveness of the quencher molecule. The location of the reporter and quencher molecules can be chosen strategically such that in a nucleotide analogue, the reporter and quencher molecules are less than 20 nm, 10 nm, 7.5 nm, 6 nm, 5 nm, 4 nm, 3 nm, 1 nm, 0.8 nm, 0.6 nm, 0.4 nm or less apart.

1.2 Methods of Use

FIG. 14

The use of the nucleotide analogues of the invention (e.g., Formulae [I]-[IV]) in an improved sequencing by synthesis reaction can be introduced by reference to FIG. 14. It will be apparent to the Reader that numerous variations and alternative methods are contemplated, including variations and methods that deviate from the broad outline of FIG. 14.

FIG. 14 shows a single nucleic acid template molecule (the sequencing target) immobilized on a substrate. In practice, the present invention is used for massively parallel sequencing. Thus, in one approach, sequencing is carried out using an array of nucleic acid template molecules, which may be, for example and not limited to, an array of single molecules (see, e.g., U.S. Pat. No. 7,666,593); an array of concatemers (see, e.g., U.S. Pat. No. 8,445,194), or an array of clonal amplification products. See generally Shendure and Ji, 2008 "Next-generation DNA sequencing" Nature Biotechnology 26:1135-45.

Figure 14A:
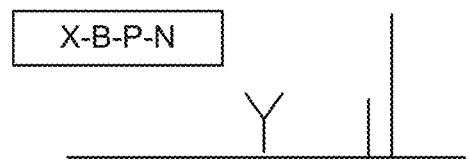
FIGS. 14A-E show steps of a sequencing-by-synthesis method using nucleotide analogues.

FIG. 14(A) shows a nucleotide analogue of the invention. Referring to Formula [I], for simplicity in this discussion X is a fluorescent dye, B is an antigen, [Q-K] is an oligophosphate, which is both a quencher for X and a cleavable linking moiety (substrate for alkaline phosphatase), and N is a deoxyribonucleotide linked to the oligophosphate. Accordingly, the nucleotide analogue in FIG. 14 has Structure [1a], wherein P is tetraphosphate.

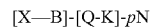
[X—B]-[Q-K]-$p$N        [I]

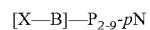
[X—B]—$P_{2-9}$-$p$N        [Ia]

The array is combined with reagents for sequencing-by-synthesis, including a DNA polymerase and a phosphatase.

Figure 14B:
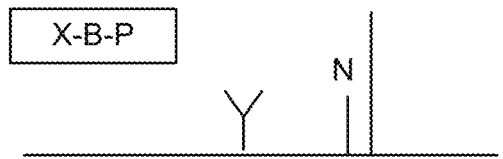

FIG. 14(B) illustrates incorporation of pN by the action of a polymerase. In some embodiments, each complementary strand is extended by at most one nucleotide analogue (per cycle) because pN comprises a reversible blocking group that prevents further polymerization. The incorporation reaction produces a fragment having the structure X—B—$P_{2-9}$, in which X is unquenched.

Figure 14C:
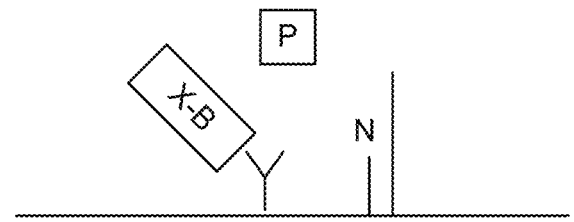

FIG. 14(C) illustrates that after the first round of incorporation, the incorporated nucleotide analogue is exposed to a cleaving agent, alkaline phosphatase, resulting in cleavage at K and producing a fragment comprising X and B, referred to as the tag element. The tag element diffuses away from the incorporated nucleotide analogue and is captured by (e.g., bound by) a capture element. In FIG. 14, the capture element is an antibody that recognizes an epitope of B and therefore specifically binds [X—B]. More generally, in this disclosure, the capture element usually comprises a binding moiety, B' ("B prime"), which is an anti-ligand of B. It will be understood that although B and B' can be referred to as a ligand-antiligand pair, a more precise characterization is that the capture element, comprising B', captures the tag element, comprising B.

In the embodiment of FIG. 14, the capture element is immobilized or confined at a position close to the template nucleic acid (e.g., on the same substrate as and adjacent to, the template nucleic acid) such that a binding event at a given capture element(s) can be associated with the nearby capture moiety(s). For any given template nucleic acid (or concatemer or clonal populations of amplicons, etc.) in the array, one of more certain capture elements will be close to, or associated with, the immobilized template nucleic acid such that the released fragment has a high likelihood of being captured close to the template.

Figure 14D:
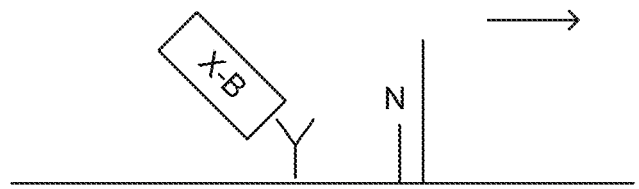

FIG. 14(D) illustrates that following the incorporation, cleavage and binding of the tag element to the capture element, excess reagents, unincorporated nucleotide analogues, and unbound fragments are washed away.

Figure 14E:
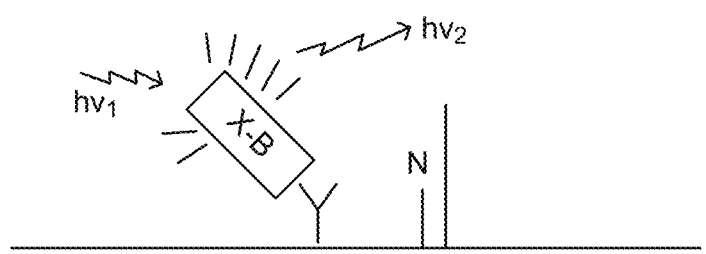

FIG. 14(E) illustrates that the signal from X can be detected and associated with incorporation of pN into the strand complementary to the template.

Additional rounds of sequencing can be carried out which may involve, inter alia, removing blocking moieties, removing tag elements and/or capture elements, and the like.

FIG. 1

Also useful for introducing the invention is the embodiment illustrated in FIG. 1, showing a method for sequencing a nucleic acid on a substrate (e.g., a silicon chip). The legend for FIGS. 1A-D is shown in FIG. 1E. The method is depicted using an array of DNA concatemers (e.g., DNA Nano-Balls (DNBs), Complete Genomics, Inc., Mountain View, Calif.). As shown in FIG. 1A, an extension oligonucleotide (depicted in FIGS. 1A-D as a horizontal line with no vertical extensions) and an oligonucleotide having a capture element immobilized to its surface (depicted in FIGS. 1A-D as a horizontal line with vertical extensions) are added to the array and immobilized by annealing to the DNA concatemer. The extension oligonucleotide hybridizes to a "primer position." The capture element is depicted as an oligonucleotide/ antibody conjugate or a multi-unit antibody structure in FIG. 1A. The capture element allows the binding molecule to attach to the DNB structure or to a surface separate from the DNB structure (e.g., to a surface adjacent the DNB structure).

Figure 1B:
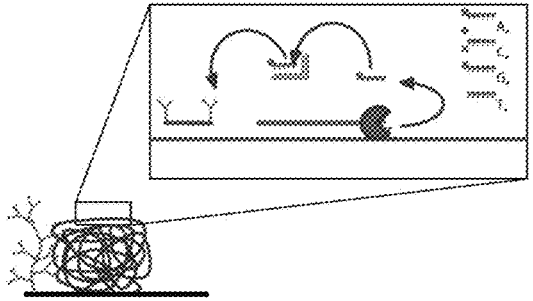

As shown in FIG. 1B, a polymerase (depicted in FIGS. 1B and 1C as a pie shape) is added to the array, along with four nucleotide analogues (A, C, G, and T). Each nucleotide analogue may contain a different detection label. Phosphatase and one or more additional quenching chemicals are also added to the array. The polymerase incorporates the nucleotide analogue that is complementary to the next nucleotide on the DNB template (e.g., adjacent to the extension oligonucleotide) and phosphatase cleaves the five-phosphate-fluorogenic dye moiety (i.e., the ligand dye complex). In FIG. 1B, a T nucleotide analogue is incorporated by the polymerase. The polymerase performs this action for a plurality of primer positions on the DNB. As described above, the blocking group on the 3'-end of the incorporated nucleotide analogue(s) prevents the polymerase from continuing to the next cycle. The fluorogenic label remains quenched at this stage.

Figure 1C:
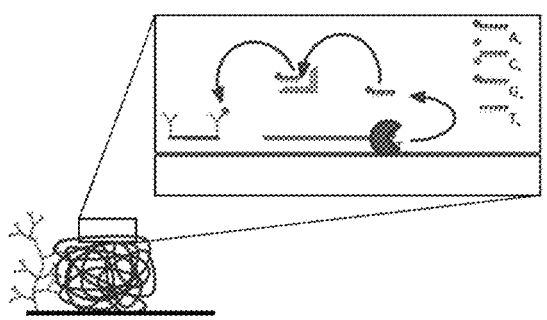

FIG. 1C shows the fragment containing the quenched dye being released by the polymerase. The phosphatase and quenching chemicals remove the quenching ability of the phosphates (i.e., the dye becomes unquenched) and also allow the unquenched label to interact with the surface through a capture element and be retained. The capture element on a DNB surface may be, for example, an oligonucleotide-antibody conjugate or a surface modified structure, such as a dendrimer comprising antibodies. It will be appreciated that any suitable ligand-antiligand pair may be used to immobilize the dye or dye conjugate. Optionally, the antibodies can be coated with fluorescence resonance energy transfer (FRET) acceptors to increase the energy transfer to the dye.

Although FIG. 1A shows both a capture oligo and a capture structure, most often only one of the capture structures will be used.

Figure 1D:
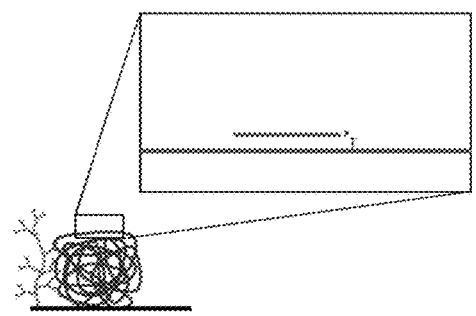
Figure 1E:
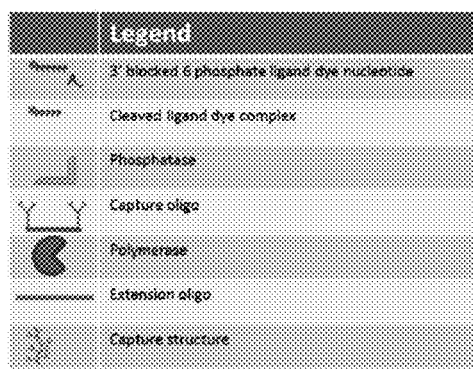
FIG. 1E is a legend for FIGS. 1A-D.

To remove the fluorescent signal and wash away the excess reagents and unincorporated nucleotide analogues from the DNB, the capture oligo can be exposed to a releasing agent that disrupts the ligand-antiligand (e.g., dye-antibody) interaction, for example, by reducing the affinity of the antibody for the bound antigen. Optionally, the delta G hybridization differential in the capture oligo and the extension oligo can be used to remove only the capture oligo. All added reagents (e.g., excess quenching chemicals) are removed during the wash step as well. After all reagents from the former cycle have been removed, the blocking group is then removed. For example, a chemical agent can be added to the array to remove the blocking group from the extended extension oligo (e.g., extended primer), resulting in a 3'-hydroxyl group. As shown in FIG. 1D, the array is ready for the repetition of this cyclic process.

Numerous Variations

It will be apparent to the Reader that numerous variations and alternative methods are contemplated, including variations and methods that deviate from the broad outline of FIGS. 1 and 14. Certain aspects of the invention are discussed in greater detail below.

The methods for sequencing a target nucleic acid include providing a template nucleic acid, a primer, a polymerase, and a nucleotide analogue.

Template Nucleic Acid

In various embodiments, the template polynucleotide is DNA (e.g., cDNA, genomic DNA, or amplification products) or RNA. In various embodiments, the polynucleotide is double stranded or single stranded.

In some embodiments, the template nucleic acid is immobilized on a solid surface. In some embodiments, the template nucleic acid is immobilized on a substrate (e.g., a bead, flow cell, pad, channel in a microfluidic device and the like). The substrate may comprise silicon, glass, gold, a polymer, PDMF, and the like.

In some embodiments, the template nucleic acid is immobilized or contained within a droplet (optionally immobilized on a bead or other substrate within the droplet).

In some embodiments, the template nucleic acid is an immobilized DNA concatemer comprising multiple copies of a complementary capture sequence (sometimes referred to as an "adaptor sequence" by analogy with DNBs).

Importantly, in certain drawings, illustrative embodiments, and discussions herein, the template nucleic acid is represented as a DNA concatemer, such as a DNA nanoball (e.g., a DNB; see U.S. Pat. No. 7,666,593). However, it will be understood that the method does not require a DNB, but can be any template such as, for example, a DNA concatemer, a dendrimer, a clonal population of templates (e.g., as produced by bridge amplification or Wildfire amplification) or a single polynucleotide molecule. Thus, importantly, the specification should be read as if each reference to a concatemer as a template alternatively refers to templates in other forms.

Nucleotide Analogues

Certain aspects of sequencing are described. Importantly, provided herein are methods for sequencing a target nucleic acid using the nucleotide analogues described herein. The methods disclosed herein are not limited to the particular analogues described herein, and are not limited to fluorescent detection systems, but may be broadly applied to other systems, as described below. With this in mind, for convenience and clarity, the system will be described by reference to these analogues.

Enzymes

A DNA polymerase is used to incorporate nucleotide analogues of the invention into a strand complementary to a template. Exemplary polymerases are DNA-Directed DNA polymerase (EC 2.7.7.7). For some applications, RNA-directed DNA polymerase (EC 2.7.7.49) is suitable.

In some embodiments, a phosphatase enzyme or a cleavage agent is provided to cleave the bond between the binding molecule and the terminal phosphate or between the binding molecule and the linking group. In some embodiments, the phosphatase enzyme or the cleavage agent is provided during the above-described primer extension reaction (e.g., the polymerase and phosphatase are present at the same time). In other embodiments, the phosphatase enzyme or the cleavage agent is provided after the above-described primer extension reaction. In embodiments where the nucleotide analogue contains a linking group, the bond between the binding molecule and the linking group is cleaved. In some embodiments, the linking group is a pH sensitive linking group or a UV cleavable linking group. In these embodiments, the bond between the binding molecule and the linking group can be cleaved by effecting a change in the pH of the solution or mixture containing the nucleotide analogue or by UV light treatment. In embodiments where the nucleotide analogue is a compound according to Formula II and does not contain a linking group (i.e., in the absence of a linking group), the phosphatase cleaves the bond between the binding molecule and the terminal phosphate. In embodiments where the nucleotide analogue is a compound according to Formula III or Formula IV and does not contain a linking group (i.e., in the absence of a linking group), a cleavage agent cleaves the bond between the binding molecule and the terminal phosphate. Exemplary cleavage agents include, for example, a phosphine, a reducing agent, or an oxidizer. The phosphatase or cleavage agent thus generates a fragment of the nucleotide analogue (i.e., a fragment of (II), (III), or (IV)) that includes the detection label and the binding molecule, i.e., X—B—. The released fragment can be referred to as a tag element.

In some embodiments of the invention, a phosphatase is used to generate a tag element. In some embodiments, an alkaline phosphatase (EC 3.1.3.1) is used. In some embodiments, an acid phosphatase (EC 3.1.3.2) is used. In some embodiments, a cleavage agent other than a phosphatase is used.

In some embodiments, phosphatase can be bound to DNA (e.g., to a complementary capture sequence). Optionally, quenching chemicals can be provided with the phosphatase to quench any background signal. As understood by one of skill in the art, the phosphatase and the quenching chemicals can be provided concomitantly or sequentially. The phosphatase and/or quenching chemicals remove the quenching ability of the phosphates to produce a fragment with an unquenched label.

Blocking Group

When the incorporated nucleotide analogue contains a blocking group (i.e., when $R^2$ of Formula II is a blocking group), the resulting extended primer is not capable of being further extended (i.e., subsequent incorporation by additional nucleotide analogues is blocked) until the blocking group is removed.

Blocking groups for use in DNA sequencing are well known in the art.

In some embodiments of the invention, the deoxyribose 3'-position of the nucleotide analogue is unblocked. In some embodiments, a reversible block is included at the 3'-position which may have the benefit of reducing the flow cycle numbers. In these embodiments, the polymerase can be a THERMINATOR enzyme (New England Biolabs, Inc.; Ipswich, Mass.). Alternatively, the cycle can proceed sequentially without the 3'-position block using, for example, a Taq polymerase.

The blocking group can be removed from the incorporated nucleotide analogue, thus allowing incorporation of the next base in a subsequent cycle. Optionally, the blocking group can be removed by chemical means. For example, the blocking group can be removed by an enzymatic cleavage reaction or a hydrolysis reaction. In some embodiments, the blocking group is removed by using a reducing agent such as dithiothreitol (DTT) or tris(2-carboxyethyl)phosphine (TCEP). Optionally, the blocking group is removed by changing the pH of the solution or mixture containing the incorporated nucleotide analogue. Optionally, the blocking group is removed by washing the blocking group from the incorporated nucleotide analogue using a phosphine.

Capture Elements

The tag element containing the unquenched label is capable of interacting with a capture element. The interaction between the tag element and the capture element may be any suitable ligand-anti-ligand interaction. In some embodiments, the ligand-antiligand interaction is hybridization to a nucleic acid moiety of the tag element with a complementary nucleic acid moiety of the capture element, or an interaction between the tag element with a binding moiety such as an antibody or aptamer.

The capture element may be directly or indirectly immobilized on a surface. In some embodiments, the surface can be a surface on which the template sequence is immobilized or situated. In some embodiments, the surface can be a surface other than the surface containing the template sequence.

In cases in which the tag element comprises an oligonucleotide moiety, the capture element may comprise a complementary sequence to which the oligonucleotide moiety is hybridized or bound. The complementary sequence may be referred to as a capture sequence.

In some cases, the capture element is an immobilized DNA concatemer with multiple copies of the capture sequence. In some cases, the capture sequence of a concatemer can be referred to as an anchor sequence, by analogy with DNBs used in ligation-based sequencing. Typically, the concatemer also comprises the template sequence. For example, the concatemer may comprise multiple (e.g., 50-500) copies of a monomer comprising both a template sequence and a capture sequence.

In some cases, the capture element is a dendrimer comprising multiple copies of a capture sequence. In some cases, the capture element is a cluster comprising an immobilized clonal population of polynucleotides (a product of an amplification reaction) comprising a capture sequence.

A capture element may comprise multiple copies of the moiety to which the tag element binds. For example, when the capture element is a nucleic acid concatemer, dendrimer or cluster, the capture sequence may be represented from 1 to $10^6$ times, sometimes $50$-$10^4$ times, sometimes 50-500 times.

In some embodiments, the capture element is, or comprises, an oligonucleotide that comprises from 10-100, more often 12-50, and sometimes 10 to 15 bases.

In some embodiments, the capture element includes a thio or thiol group.

In some embodiments, the capture element comprises streptavidin, an antibody, an aptamer, a protein, or a dendrimer.

The capture element may be indirectly immobilized via an intermediate structure as described in Illustrative Embodiment 5. The capture element may be immobilized before or after binding the tag element.

In some embodiments, capture elements, such as streptavidin or an antibody, may be coupled to a polymerase without interfering, with the function of the polymerase. In these examples, there is no separate step of adding a new capture element for each cycle prior to the extension reaction.

In some embodiments, the capture element is constrained within a droplet.

In some embodiments, capture elements, such as streptavidin or an antibody, may be coupled to a polymerase without interfering with the function of the polymerase. In these examples, there is no separate step of adding a new capture element for each cycle prior to the extension reaction.

Wash Steps

Optionally, following the incorporation and cleavage steps, excess reagents and unincorporated nucleotide analogues are removed (e.g., washed away) from the surface.

Detection/Imaging

The fluorescence emissions from the label of the fragment are then detected using techniques known to those of skill in the art, for example, the use of a charge-coupled device optionally in combination with filters. Exemplary detection methods include fluorescence microscopy, total internal reflection fluorescence microscopy, high inclined illumination microscopy, or parallel confocal microscopy.

Labels

In some embodiments, fewer than four detection labels are used, as described, for example, in U.S. Pat. No. 8,617,881. In some embodiments, two labels are used. In some embodiments, a single label is used, as described herein below. Single or two-color schemes (e.g., using single or two detection filters or channels) may be used.

Removal of the Tag Element

The method described herein can further include removing the tag element from the capture element on the surface.

In some embodiments, the removing step comprises heating the fragment and the capture element. In some embodiments, the removing step includes washing the fragment-capture element complex with a buffer or with a hybridization disrupting agent (e.g., formamide). Optionally, the buffer has a low salt content to disrupt hybridization. In designing the elements of a sequencing system of the invention, a person of ordinary skill in the art will select washing steps that disrupt certain interactions without disrupting other interactions. For example, systems may be designed to avoid disrupting the association of the template being sequenced and extended primer. In some embodiments, the removing step includes adding an enzyme to cleave the fragment from the capture element on the surface. In some embodiments, the removing step includes adding a reducing agent or a displacement agent to remove the fragment from the capture element on the surface.

2. 3'-O— Modified Terminal Phosphate-Labeled Cleavable Nucleotide Analogues

Described herein are 3'-O— modified terminal phosphate-labeled cleavable nucleotide analogues suitable for use in a starless-stepwise sequencing-by-synthesis approach.

Advantages of the nucleotide analogues described herein, in contrast to other reversible terminators, include the elimination of a scar which results in faster and more efficient incorporation, an easier synthetic process, and the absence of, or reduced, fluorescent background and quenching of the dye by the phosphate. Due to absence of a fluorescent background, a very high concentration of nucleotides can be used to drive the 3'-O— modified terminal phosphate-labeled nucleotides incorporation to completion in a very short amount of time, which in return eliminates the subsequent "fill-in" reaction step by unlabeled reversible terminators used in sequencing-by-synthesis. In one approach, a mixture of nucleotides with the 3' blocking group but lacking the additional phosphates and dye is mixed with the dye labeled molecules, or followed in a chase reaction, to fill in any sites that have not extended during that cycle.

The nucleotide analogues useful in the methods described herein include compounds represented by Formula II:

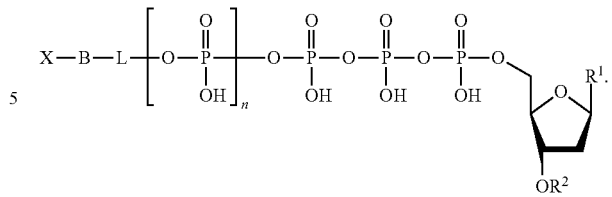

In Formula II, n is 0, 1, 2, 3, 4, 5, 6, or 7.

Also in Formula II, L is absent or a linking group. In some embodiments, L is a linking group selected from a substituted or unsubstituted alkyl, substituted or unsubstituted alkenyl, or substituted or unsubstituted aryl. For example, the linking group can be a methylene group or a substituted phenyl group. In some embodiments, the linking group further comprises a quencher, examples of which are known in the art and described hereinabove, which is represented as "Q" herein.

Additionally in Formula II, $R^1$ is a nitrogenous base suitable for use as a nucleoside base. For example, $R^1$ can be a base selected from the group consisting of adenine (A), cytosine (C), guanine (G), thymine (T), uracil (U), and derivatives of these.

Further in Formula II, $R^2$ is hydrogen or a blocking group. As used herein, the term "blocking group" refers to any group that can be cleaved to provide a hydroxyl group at the 3'-position of the nucleotide analogue. The blocking group can be cleavable by physical means, chemical means, heat, and/or light. Optionally, the blocking group is cleavable by enzymatic means. In some embodiments, the blocking group is an amino-containing blocking group (e.g., —$NH_2$). In some embodiments, the blocking group is an allyl-containing blocking group (e.g., —$CH_2CH$=$CH_2$). In some embodiments, the blocking group is an azido-containing blocking group (e.g., —$CH_2N_3$). In some embodiments, the blocking group is an alkoxy-containing blocking group (e.g., —$CH_2OCH_3$). In some embodiments, the blocking group is polyethylene glycol (PEG). In some embodiments, the blocking group is a substituted or unsubstituted alkyl (i.e., a substituted or unsubstituted hydrocarbon).

Also in Formula II, B is a binding molecule. As used herein, the term "binding molecule" refers to the portion of the nucleotide analogue that, upon cleavage from the linking group, if present, or from the phosphate moiety when the linking group is absent, interacts with a capture element as described herein. In some embodiments, the binding molecule is biotin, an antibody, an amino acid, cholesterol, fluorescein isothiocyanate, or a peptide. Optionally, the binding molecule contains a thio (—S—) or a thiol (—SH) moiety. Optionally, the binding molecule contains an oligonucleotide.

Further in Formula II, X is a detection label as described above.

Examples of nucleotide analogues according to Formula II include the following:

Compound 1

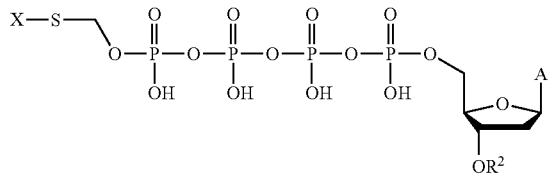

Compound 2

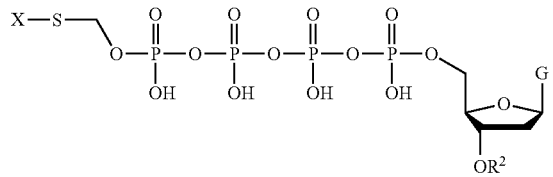

-continued
Compound 3
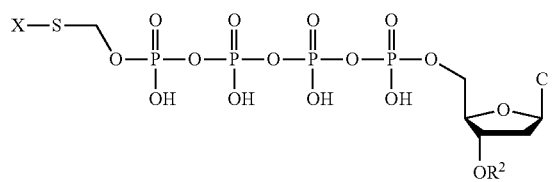
Compound 4
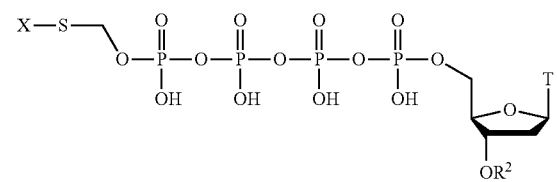
Compound 5
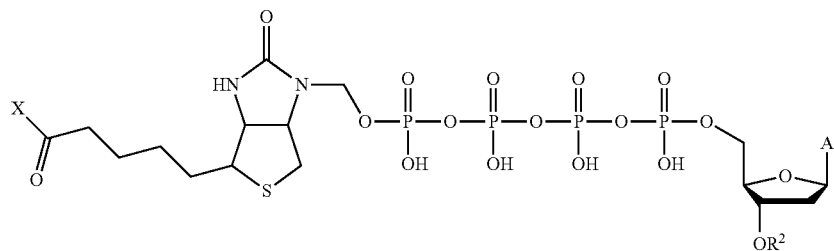
Compound 6
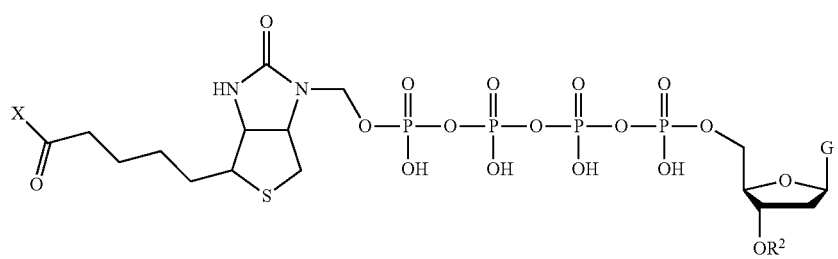
Compound 7
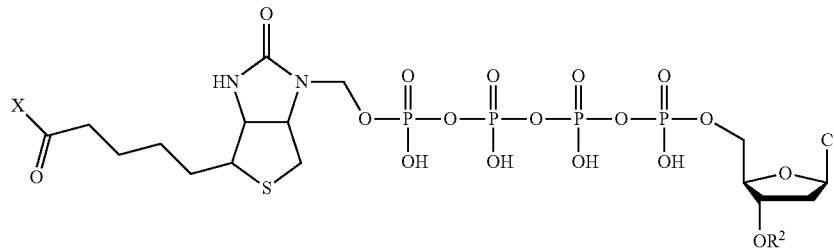
Compound 8
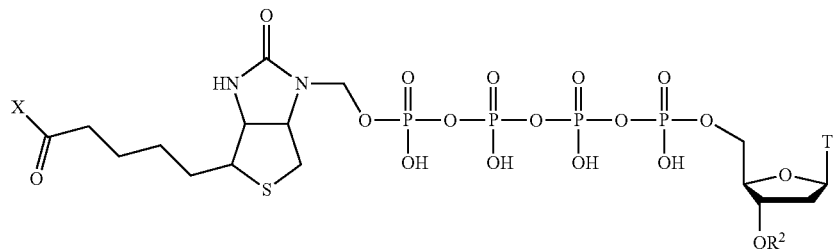

In alternative embodiments, the nucleotide analogue according to Formula II is a compound similar to Compound 1, Compound 2, Compound 3, Compound 4, Compound 5, Compound 6, Compound 7, or Compound 8 that contains three phosphate groups (i.e., n=0).

The nucleotide analogues useful in the methods described herein also include compounds represented by Formula III:

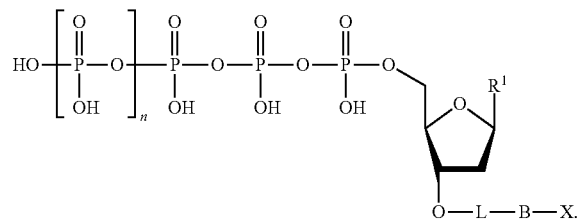

In Formula III, n is 0, 1, 2, 3, 4, 5, 6, or 7.

Also in Formula III, L is absent or a linking group. In some embodiments, L is a linking group selected from a substituted or unsubstituted alkyl, substituted or unsubstituted alkenyl, or substituted or unsubstituted aryl. For example, the linking group can be a methylene group or a substituted phenyl group. In some embodiments, the linking group further comprises a quencher, which is represented as "Q" herein. For example, the quencher can be dimethylaminozobenzenesulfonic acid; a BLACK HOLE QUENCHER dye, commercially available from Biosearch Technologies (Petaluma, Calif.); QXL Quenchers, commercially available from AnaSpec, Inc. (Fremont, Calif.); quenchers commercially available from Integrated DNA Technologies (Coralville, Iowa) under the IOWA BLACK product line, including IOWA BLACK FQ and IOWA BLACK RQ; and IRDYE QC-1, commercially available from LI-COR Biosciences (Lincoln, Nebr.).

Additionally in Formula III, $R^1$ is a nitrogenous base suitable for use as a nucleoside base. For example, $R^1$ can be a base selected from the group consisting of adenine (A), cytosine (C), guanine (G), thymine (T), uracil (U), and derivatives of these.

Also in Formula III, B is a binding molecule. As used herein, the term "binding molecule" refers to the portion of the nucleotide analogue that, upon cleavage from the linking group, if present, or from the phosphate moiety when the linking group is absent, interacts with a capture element as described herein. In some embodiments, the binding molecule is biotin, an antibody, an amino acid, cholesterol, fluorescein isothiocyanate, or a peptide. Optionally, the binding molecule contains a thio (—S—) or a thiol (—SH) moiety. Optionally, the binding molecule contains an oligonucleotide.

Further in Formula III, X is a detection label. In some embodiments, the detection label is a molecule containing a charged group (e.g., a molecule containing a cationic group or a molecule containing an anionic group), a fluorescent molecule (e.g., a fluorescent dye), a fluorogenic molecule, or a metal. Optionally, the detection is a fluorogenic label. A fluorogenic label can be any label that is capable of emitting light when in an unquenched form (e.g., when not quenched by another agent). The fluorescent moiety emits light energy (i.e., fluoresces) at a specific emission wavelength when excited by an appropriate excitation wavelength. When the fluorescent moiety and a quencher moiety are in close proximity, light energy emitted by the fluorescent moiety is absorbed by the quencher moiety. Optionally, the detection label is a fluorogenic dye. In some embodiments, the fluorogenic dye is a fluorescein, a rhodamine, a phenoxazine, an acridine, a coumarin, or a derivative thereof. In some embodiments, the fluorogenic dye is a carboxyfluorescein. Further examples of suitable fluorogenic dyes include the fluorogenic dyes commercially available under the ALEXA FLUOR product line (Life Technologies; Carlsbad, Calif.). The fluorogenic dye can also be a dye as described, for example, in Grimm et al., 2013, *Progress in Molecular Biology and Translational Science*, Vol. 113, Chapter 1, pages 1-34. Optionally, the label is a redoxgenic label. Optionally, the label is a reduction tag, a thio-containing molecule, or a substituted or unsubstituted alkyl.

Examples of nucleotide analogues according to Formula III include the following:

Compound 9

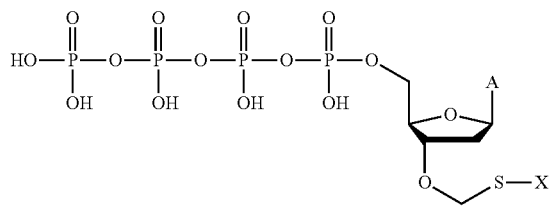

Compound 10

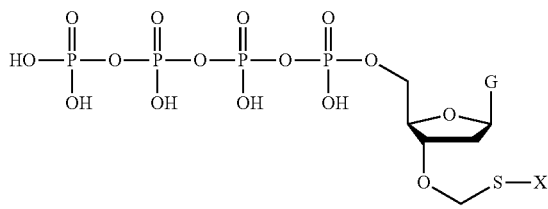

Compound 11

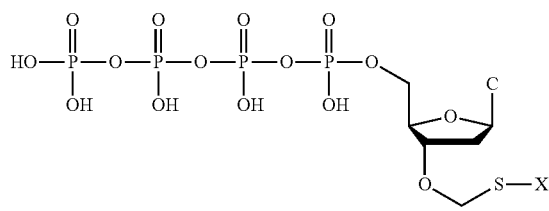

Compound 12

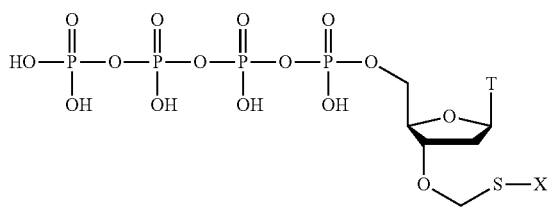

-continued

Compound 13

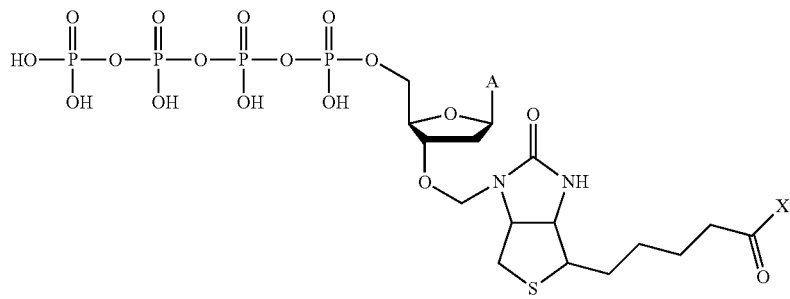

Compound 14

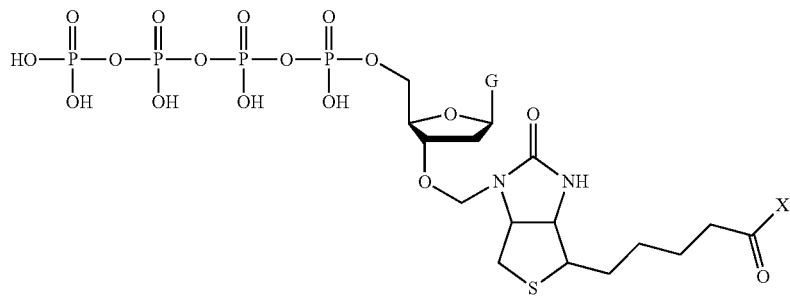

Compound 15

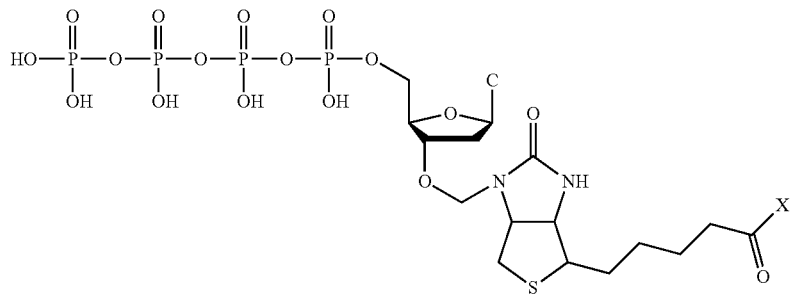

Compound 16

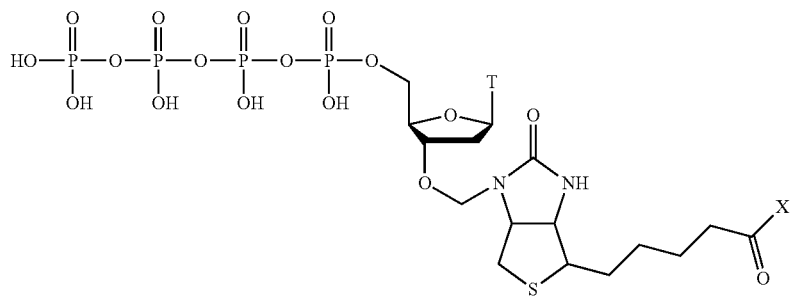

In alternative embodiments, the nucleotide analogue according to Formula III is a compound similar to Compound 9, Compound 10, Compound 11, Compound 12, Compound 13, Compound 14, Compound 15, or Compound 16 that contains three phosphate groups (i.e., n=0).

The nucleotide analogues useful in the methods described herein also include compounds represented by Formula IV:

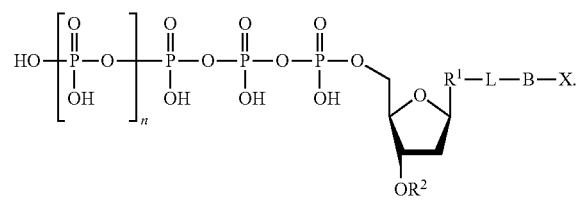

In Formula IV, n is 0, 1, 2, 3, 4, 5, 6, or 7.

Also in Formula IV, L is absent or a linking group. In some embodiments, L is a linking group selected from a substituted or unsubstituted alkyl, substituted or unsubstituted alkenyl, or substituted or unsubstituted aryl. For example, the linking group can be a methylene group or a substituted phenyl group. In some embodiments, the linking group further comprises a quencher, which is represented as "Q" herein. For example, the quencher can be dimethylaminozobenzenesulfonic acid; a BLACK HOLE QUENCHER dye, commercially available from Biosearch Technologies (Petaluma, Calif.); QXL Quenchers, commercially available from AnaSpec, Inc. (Fremont, Calif.); quenchers commercially available from Integrated DNA Technologies (Coralville, Iowa) under the IOWA BLACK product line, including IOWA BLACK FQ and IOWA BLACK RQ; and IRDYE QC-1, commercially available from LI-COR Biosciences (Lincoln, Nebr.).

Additionally in Formula IV, $R^1$ is a nitrogenous base suitable for use as a nucleoside base. For example, $R^1$ can be a base selected from the group consisting of adenine (A), cytosine (C), guanine (G), thymine (T), uracil (U), and derivatives of these.

Further in Formula IV, $R^2$ is hydrogen or a blocking group. As used herein, the term "blocking group" refers to any group that can be cleaved to provide a hydroxyl group at the 3'-position of the nucleotide analogue. The blocking group can be cleavable by physical means, chemical means, heat, and/or light. Optionally, the blocking group is cleavable by enzymatic means. In some embodiments, the blocking group is an amino-containing blocking group (e.g., —$NH_2$). In some embodiments, the blocking group is an allyl-containing blocking group (e.g., —$CH_2CH=CH_2$). In some embodiments, the blocking group is an azido-containing blocking group (e.g., —$CH_2N_3$). In some embodiments, the blocking group is an alkoxy-containing blocking group (e.g., —$CH_2OCH_3$). In some embodiments, the blocking group is polyethylene glycol (PEG). In some embodiments, the blocking group is a substituted or unsubstituted alkyl (i.e., a substituted or unsubstituted hydrocarbon).

Also in Formula IV, B is a binding molecule. As used herein, the term "binding molecule" refers to the portion of the nucleotide analogue that, upon cleavage from the linking group, if present, or from the phosphate moiety when the linking group is absent, interacts with a capture element as described herein. In some embodiments, the binding molecule is biotin, an antibody, an amino acid, cholesterol, fluorescein isothiocyanate, or a peptide. Optionally, the binding molecule contains a thio (—S—) or a thiol (—SH) moiety. Optionally, the binding molecule contains an oligonucleotide.

Further in Formula IV, X is a detection label. In some embodiments, the detection label is a molecule containing a charged group (e.g., a molecule containing a cationic group or a molecule containing an anionic group), a fluorescent molecule (e.g., a fluorescent dye), a fluorogenic molecule, or a metal. Optionally, the detection is a fluorogenic label. A fluorogenic label can be any label that is capable of emitting light when in an unquenched form (e.g., when not quenched by another agent). The fluorescent moiety emits light energy (i.e., fluoresces) at a specific emission wavelength when excited by an appropriate excitation wavelength. When the fluorescent moiety and a quencher moiety are in close proximity, light energy emitted by the fluorescent moiety is absorbed by the quencher moiety. Optionally, the detection label is a fluorogenic dye. In some embodiments, the fluorogenic dye is a fluorescein, a rhodamine, a phenoxazine, an acridine, a coumarin, or a derivative thereof. In some embodiments, the fluorogenic dye is a carboxyfluorescein. Further examples of suitable fluorogenic dyes include the fluorogenic dyes commercially available under the ALEXA FLUOR product line (Life Technologies; Carlsbad, Calif.). Optionally, the label is a redoxgenic label. Optionally, the label is a reduction tag, a thio-containing molecule, or a substituted or unsubstituted alkyl.

Examples of nucleotide analogues according to Formula IV include the following:

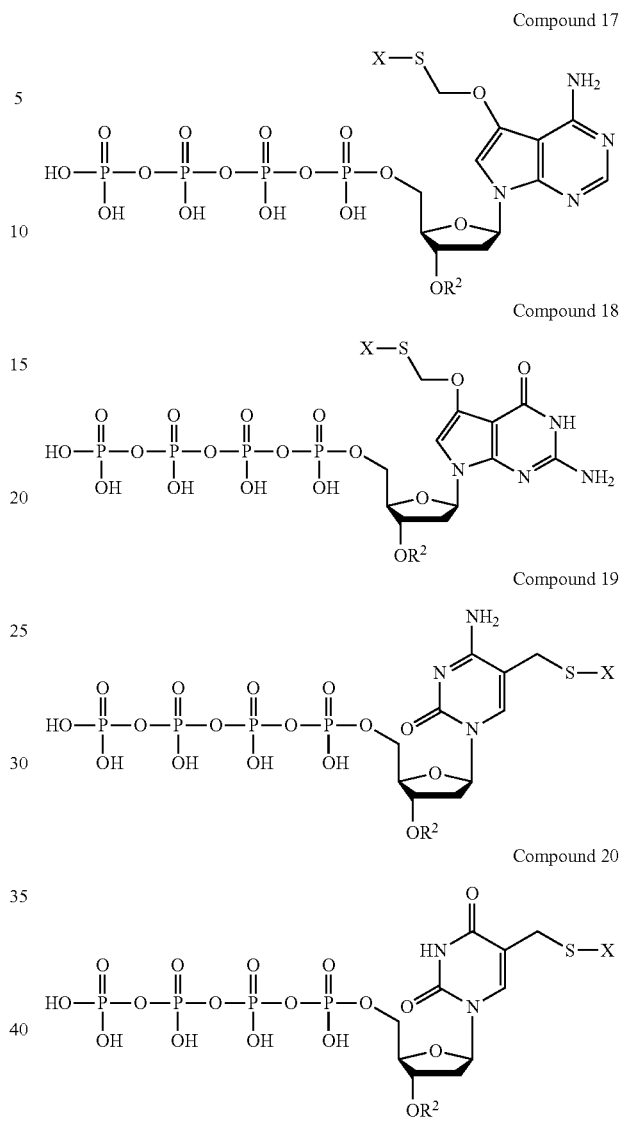

In alternative embodiments, the nucleotide analogue according to Formula IV is a compound similar to Compound 17, Compound 18, Compound 19, or Compound 20 that contains three phosphate groups (i.e., n=0).

Further examples of suitable nucleotide analogues are depicted in FIGS. 1-14.

The compounds described herein can be prepared in a variety of ways known in the art of organic synthesis or variations thereon as appreciated by those skilled in the art. The compounds described herein can be prepared from readily available starting materials. Optimum reaction conditions may vary with the particular reactants or solvents used, but such conditions can be determined by one skilled in the art.

Variations on Formula I, Formula II, Formula III, and Formula IV and the compounds described herein include the addition, subtraction, or movement of the various constituents as described for each compound. Similarly, when one or more chiral centers are present in a molecule, the chirality of the molecule can be changed. Additionally, compound synthesis can involve the protection and deprotection of various chemical groups. The use of protection and deprotection and the selection of appropriate protecting groups can be determined by one skilled in the art. The chemistry of protecting groups can be found, for example, in Wuts and Greene, Protective Groups in Organic Synthesis, 4th Ed., Wiley & Sons, 2006, which is incorporated herein by reference in its entirety. The synthesis and subsequent testing of various compounds as described herein to determine efficacy is contemplated.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

Optionally, the compounds described herein can be synthesized by using commercially available dNTPs. The commercially available dTNPs can be conjugated to a linker or a binding molecule through a phosphate conjugation reaction. The 3'-position of the dNTPs can be blocked by reacting the compounds with a protecting group. The conjugating and blocking reactions can be performed in any order.

Provided herein are methods for sequencing a target nucleic acid using the nucleotide analogues described herein. The methods disclosed herein are not limited to the particular analogues described herein, and are not limited to fluorescent detection systems, but may be broadly applied to other systems, as described below. With this in mind, for convenience and clarity, the system will be described by reference to these analogues.

In the present method, the identity of a nucleotide analogue is detected after the nucleotide analogue is incorporated into a polynucleotide by a primer extension reaction. In one approach, sequencing a target nucleic acid includes the following steps: (1) providing a template nucleic acid, a primer, a polymerase, and a nucleotide analogue as described herein; (2) extending the primer by incorporating the nucleotide analogue (and optionally other nucleotides); (3) providing a phosphatase to cleave the incorporated nucleotide analogue between the binding molecule and the terminal phosphate (in the absence of a linking group) or between the binding molecule and the linking group (in the presence of a linking group), thereby generating a fragment of Formula II, Formula III, or Formula IV comprising the label and the binding molecule, wherein the label is unquenched; (4) binding the fragment to a capture element immobilized on a surface; and (5) detecting a fluorescence emission from the label of the fragment captured on the surface. Each step is further described below.

The methods for sequencing a target nucleic acid include providing a template nucleic acid, a primer, a polymerase, and a nucleotide analogue.

Optionally, the nucleotide analogue provided is a mixture of four nucleotide analogues according to Formula II, Formula III, or Formula IV, each including a different base (i.e., a different $R^1$ group). In some embodiments, each of the four nucleotide analogues comprises a different detection label (i.e., a different X group). For example, the mixture of nucleotide analogues according to Formula II can include the following compounds:

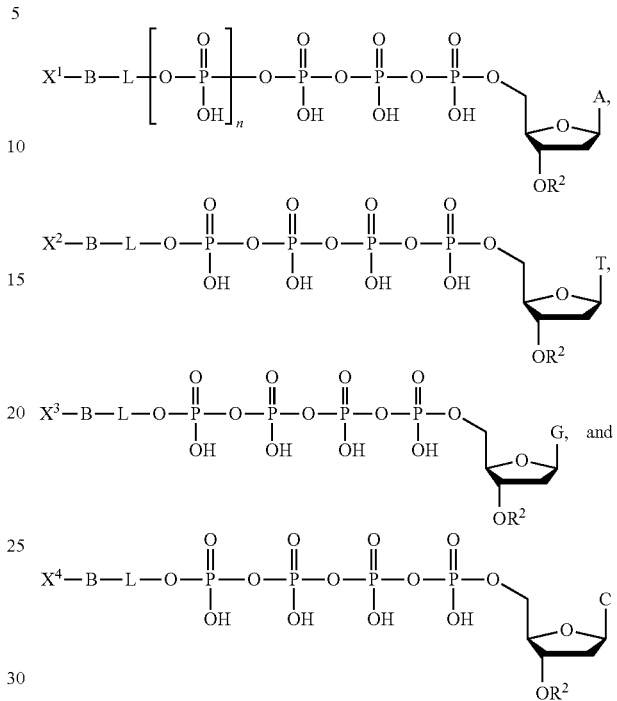

wherein each of $X^1$, $X^2$, $X^3$, and $X^4$ represents distinct detection labels. In some embodiments, one or more different or additional bases is used such as U (uracil) or I (inosine). In some embodiments, the labels are quenched by their proximity to the phosphates.

As noted above, in some embodiments, fewer than four detection labels are used, as described, for example, in U.S. Pat. No. 8,617,881. In some embodiments, two labels are used. In some embodiments, a single label is used, as described herein below.

The polymerase enzyme incorporates a nucleotide analogue into a nucleic acid, thus extending the primer. When the incorporated nucleotide analogue contains a blocking group (i.e., when $R^2$ is a blocking group), the resulting extended primer is not capable of being further extended (i.e., subsequent incorporation by additional nucleotide analogues is blocked) until the blocking group is removed.

Optionally, a phosphatase enzyme is provided to cleave the bond between the binding molecule and the terminal phosphate or between the binding molecule and the linking group. In some embodiments, the phosphatase enzyme is provided during the above-described primer extension reaction. In other embodiments, the phosphatase enzyme is provided after the above-described primer extension reaction. In embodiments where the nucleotide analogue is a compound according to Formula II and does not contain a linking group (i.e., in the absence of a linking group), the phosphatase cleaves the bond between the binding molecule and the terminal phosphate. The phosphatase thus generates a fragment of the nucleotide analogue (i.e., a fragment of (II), (III), or (IV)) that includes the detection label and the binding molecule, i.e., X—B—.

In some embodiments, a cleavage agent is provided to generate the fragment of the nucleotide analogue that includes the detection label and the binding molecule. In embodiments where the nucleotide analogue is a compound according to Formula III or Formula IV, the detection label and the binding molecule can be released from the nucleotide analogue by a cleavage agent as described herein (e.g., by a phosphine, TCEP, DTT, or a reducing agent). This cleavage allows the epitope of the binding molecule to be exposed in a form that can be recognized by a capture element in the capture methods described herein.

In some embodiments, phosphatase can be bound to DNA (e.g., to a complementary capture sequence). Optionally, quenching chemicals can be provided with the phosphatase to quench any background signal. As understood by one of skill in the art, the phosphatase and the quenching chemicals can be provided concomitantly or sequentially. The phosphatase and/or quenching chemicals remove the quenching ability of the phosphates to produce a fragment with an unquenched label. The unquenched label of the fragment emits light.

3. Systems

The invention provides systems and kits for practicing the methods described herein. Exemplary kits comprise one or more of nucleotide analogues, capture elements, or enzymes described herein. Systems of the invention may comprise a substrate comprising immobilized capture elements.

4. Illustrative Embodiments

The examples below are intended to further illustrate certain aspects of the methods and compositions described herein, and are not intended to limit the scope of the claims.

Illustrative Embodiment 1: Production of Fluorescent Molecules

Figure 2:
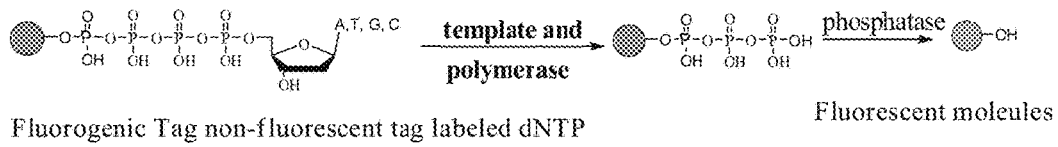
FIG. 2 shows a scheme depicting the conversion of a nucleotide analogue into a fluorescent molecule.

FIG. 2 illustrates a nucleotide analogue as described herein comprising a fluorescent tag. As shown in FIG. 2, a polymerase incorporates the nucleotide into the extended polynucleotide, resulting in release of a fragment comprising the fluorescent molecule and tri-phosphate. The fluorescence is quenched by the triphosphate group. A phosphatase then cleaves the fluorogenic tag from the terminal phosphate, resulting in a tag comprising an unquenched fluorescent molecule.

Illustrative Embodiment 2: Droplets Containing DNBs

Figure 3:
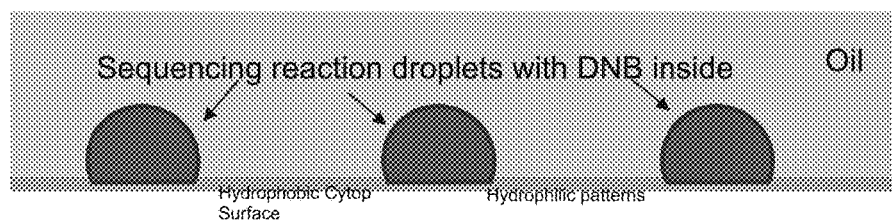
FIG. 3 shows a cartoon of droplets containing an immobilized DNA concatemer and including multiple copies of a complementary capture sequence.

The sequencing-by-synthesis methods using the nucleotide analogues as described herein can be performed within droplets. FIG. 3 illustrates droplets positioned on hydrophilic regions of a high density array of hydrophilic regions ("spots") surrounded by hydrophobic surface. See U.S. Pat. No. 7,666,593; Drmanac et al., 2010, Science 327(5961): 78-81. An exemplary hydrophobic surface comprises Cytop, an amorphous fluoropolymer (Bellex International Corporation, Wilmington, Del.). It will be recognized that upon addition of an aqueous solution to such a surface, droplets are spontaneously formed. The sequencing reactions described herein can be performed within droplets containing the DNA template and a capture element. The DNA template may be immobilized on the array surface or on a bead within the droplet. An exemplary feature of this system is that the droplet constrains diffusion of reagents, including the tag element which can be captured by capture elements within the droplet. In one embodiment, the DNA template is an immobilized DNA concatemer which includes multiple copies of a capture sequence (capture element). For example, a concatemer is immobilized on a surface by the interaction between the DNA and the coating on the surface. Optionally, a concatemer can be immobilized on beads or other substrate within the droplet. At the completion of the polymerization-capture cycle, the array surface may be washed as described herein.

Figure 4:
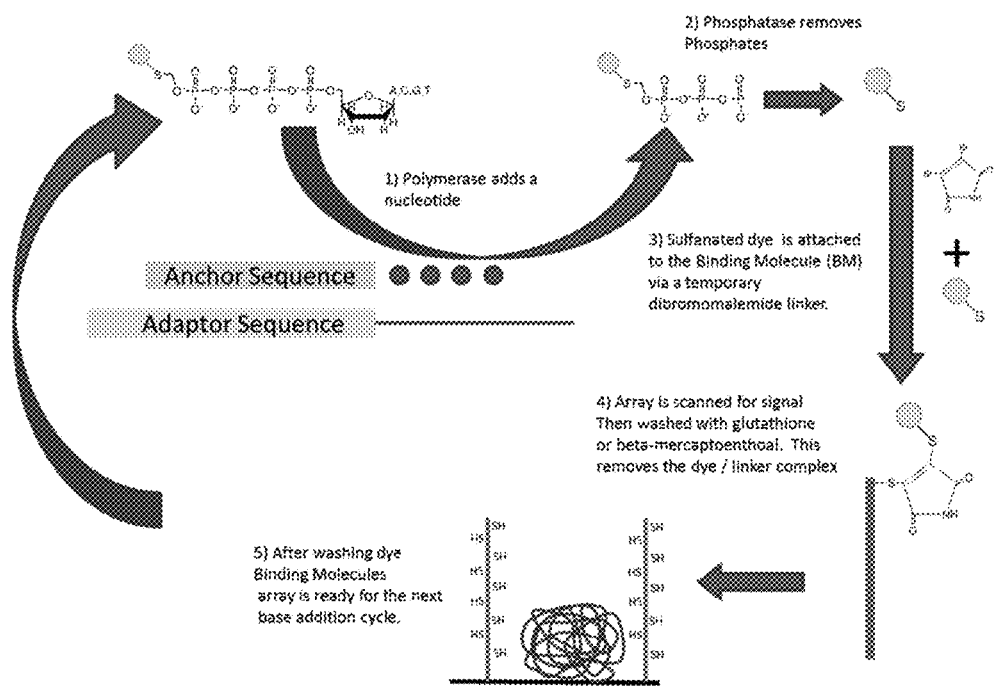
FIG. 4 is a scheme showing the sequencing-by-synthesis method using nucleotide analogues where the fluorescent fragment is attached to the surface of an array through a transient dibromomaleimide linker.

Illustrative Embodiment 3: Surface Capturing Using Reversible Transient Linkers FIG. 4 illustrates one sequencing approach according to the invention in which the tag element and terminal phosphate are linked by a sulfur-oxygen bond. Incorporation of the nucleotide by polymerase, and treatment with phosphatase produces thio-containing tag element (e.g., a sulfanated fluorescent dye) which may be attached to a Binding Molecule (B), optionally via a reversible linker. Alternatively, the thio-containing tag element is attached directly to a capture element via a reversible linker. In one approach, as illustrated in FIG. 4, the thio-containing tag element reacts with dibromomaleimide to produce a reversible transient linker. The fluorescent thio-containing fragment and dibromomaleimide complex then binds to the capture element immobilized on a surface. In this example, the capture element comprises a thiol-polymer, such as BSA (comprising 35 cysteine residues). The array is then scanned for a signal using a detector and the array is washed with glutathione or beta-mercaptoethanol to remove the fluorescent thio-containing fragment and dibromomaleimide complex. Exemplary redox genic tags useful in methods of the invention are described in US Pat Pub. 20140001055.

Figure 5:
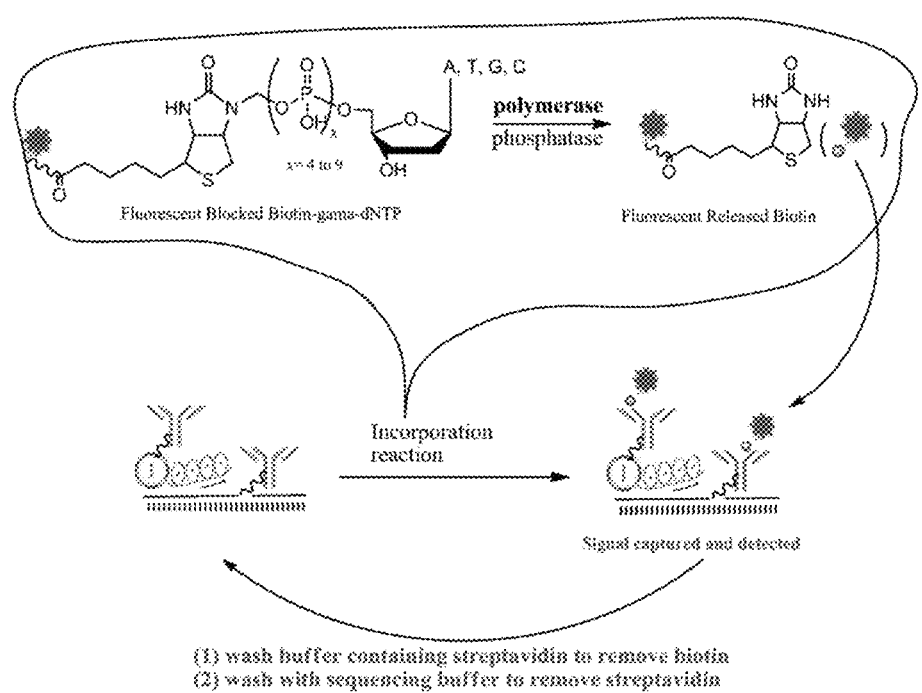
FIG. 5 is a scheme showing the sequencing-by-synthesis method using nucleotide analogues that contain biotin as the binding molecule. The capture element in this scheme is bound to the 5'-end of the primer.

Illustrative Embodiment 4: Surface Capturing Through Capture Element at 5'-End of Primer FIG. 5 depicts an embodiment in which the capture element is bound to the 5'-end of the primer (rather than, for example, the array surface). In this configuration, the capture element is closer to the nucleotide incorporation site, thus providing for a more efficient capture of the tag element. Without intending to be bound by a particular mechanism, rapid dephosphorylation of the tag element-phosphate complex minimizes diffusion before the tag element is captured. In FIG. 5, biotin is used as the binding molecule in a nucleotide analogue.

At the completion of the cycle, following detection of the captured signal, the array is regenerated by using a wash buffer containing streptavidin to remove biotin, and then washed with a sequencing buffer to remove the streptavidin.

Figure 6:
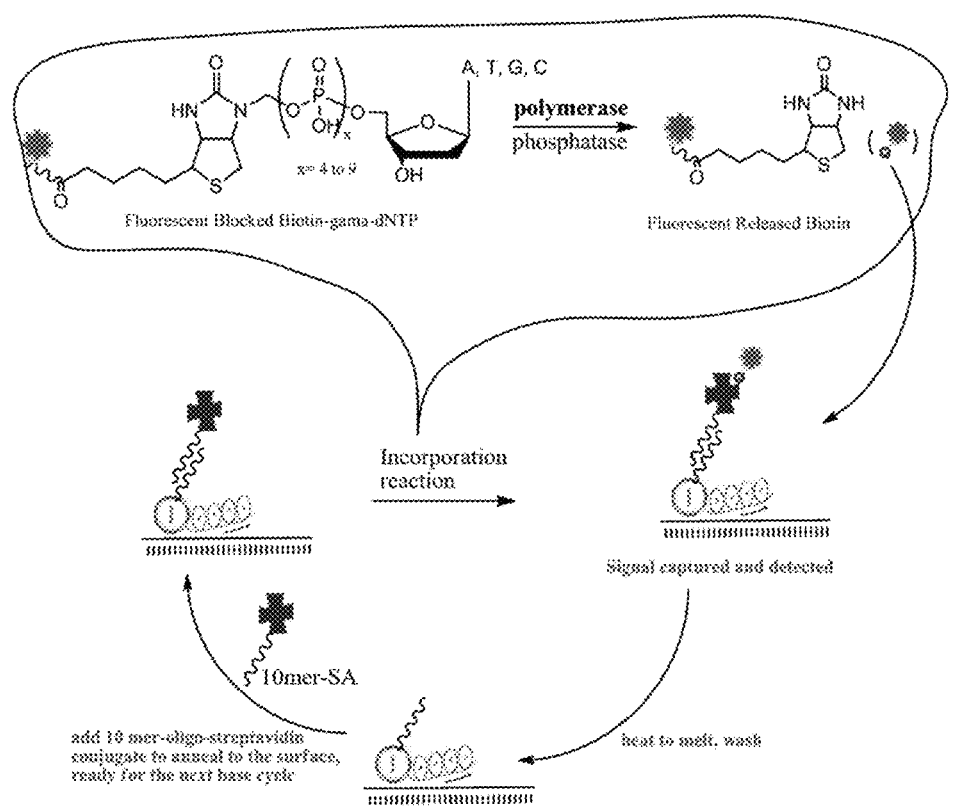
FIG. 6 is a scheme showing the sequencing-by-synthesis method using nucleotide analogues that contain biotin as the binding molecule. The capture element in this scheme is bound to an oligonucleotide at the 5'-end of the primer.

Illustrative Embodiment 5: Surface Capturing Through Capture Element Bound to Oligonucleotides at 5'-End of Primer FIG. 6 depicts a sequencing method where the capture element is a conjugate of first member of a ligand-antiligand pair (e.g., streptavidin) and an oligonucleotide. The oligonucleotide on the capture element is complementary to a second oligonucleotide immobilized on the array or bead surface, or attached to the sequencing primer. Capture of the tag element occurs when the tag fragment (here shown comprising biotin) binds the antiligand of the capture element (here shown as streptavidin) and the oligonucleotide portion of the capture element is hybridized to the immobilized complementary oligonucleotide. In some embodiments, the oligonucleotide of the capture element and the immobilized complementary oligonucleotide are short, e.g., 10-50 bases, sometimes 10-15 bases.

The short oligonucleotide and the binding molecule are selected such that the binding molecule has a strong affinity for the tag element while the short oligonucleotide has a low affinity to the capture sequence (or other immobilized complementary oligonucleotide). This allows the binding molecule to be washed away at the end of the cycle.

It will be appreciated that in other embodiments in which a capture element is indirectly immobilized, the oligonucleotide portion of the capture element and the immobilized complementary oligonucleotide can be replaced with a different ligand-antiligand pair.

Illustrative Embodiment 6: Surface Capturing Through Hybridization

Figure 7:
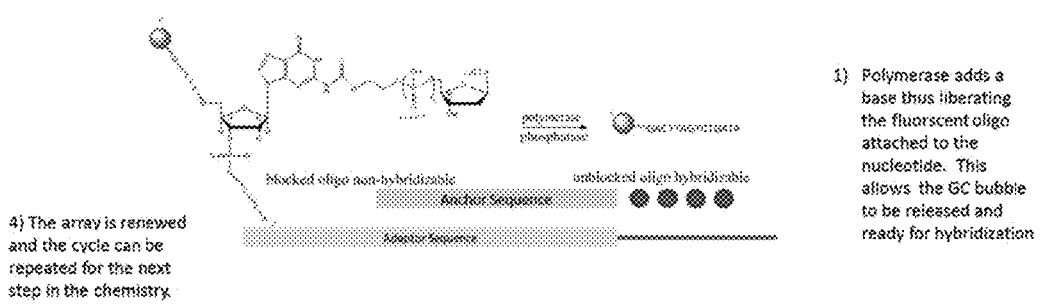
FIG. 7 is a scheme showing the sequencing-by-synthesis method where the surface capturing is performed through hybridization.
Figure 7:

FIG. 7 illustrates a nucleotide analogue in which the binding moiety of the nucleotide analogue is an oligonucleotide. In this embodiment, the nucleotide-oligophosphate is linked to the tag moiety (SEQ ID NO:1) via the oligonucleotide, rendering it non-hybridizable. In the embodiment shown in the drawing, the nucleotide-oligophosphate is linked to a guanine of the oligonucleotide via a peptide bond (i.e., a peptide nucleic acid structure). Following incorporation of the nucleotide, phosphatase is used to remove the oligophosphate.

Illustrative Embodiment 7: Surface Capturing Through Hybridization

Figure 8:
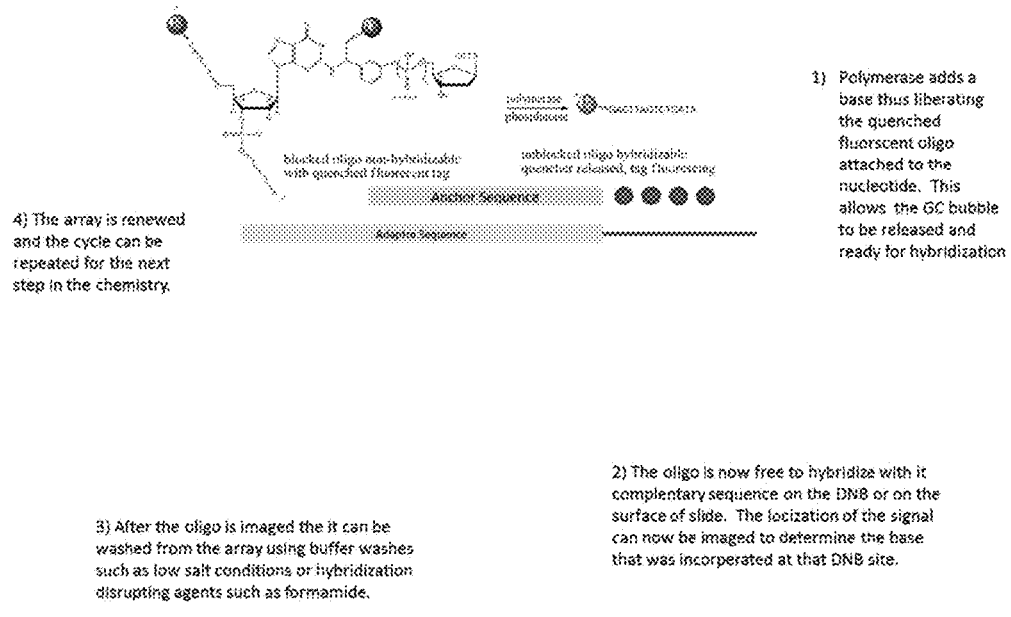
FIG. 8 is a scheme showing the sequencing-by-synthesis method where the nucleotide analogue contains a quencher and the surface capturing is performed through hybridization.
Figure 8:

FIG. 8 illustrates an embodiment in which the quencher is positioned on a cleavable linker attached to the terminal-phosphate of the analogue. In FIG. 8, the nucleotide analogue is similar to that shown in FIG. 7. However, the nucleotide analogue of FIG. 8 includes a quencher on a cleavable linker attached to the terminal-phosphate of the analogue.

Illustrative Embodiment 8: Regeneration by Removal of the Capture Element

Figure 9A:
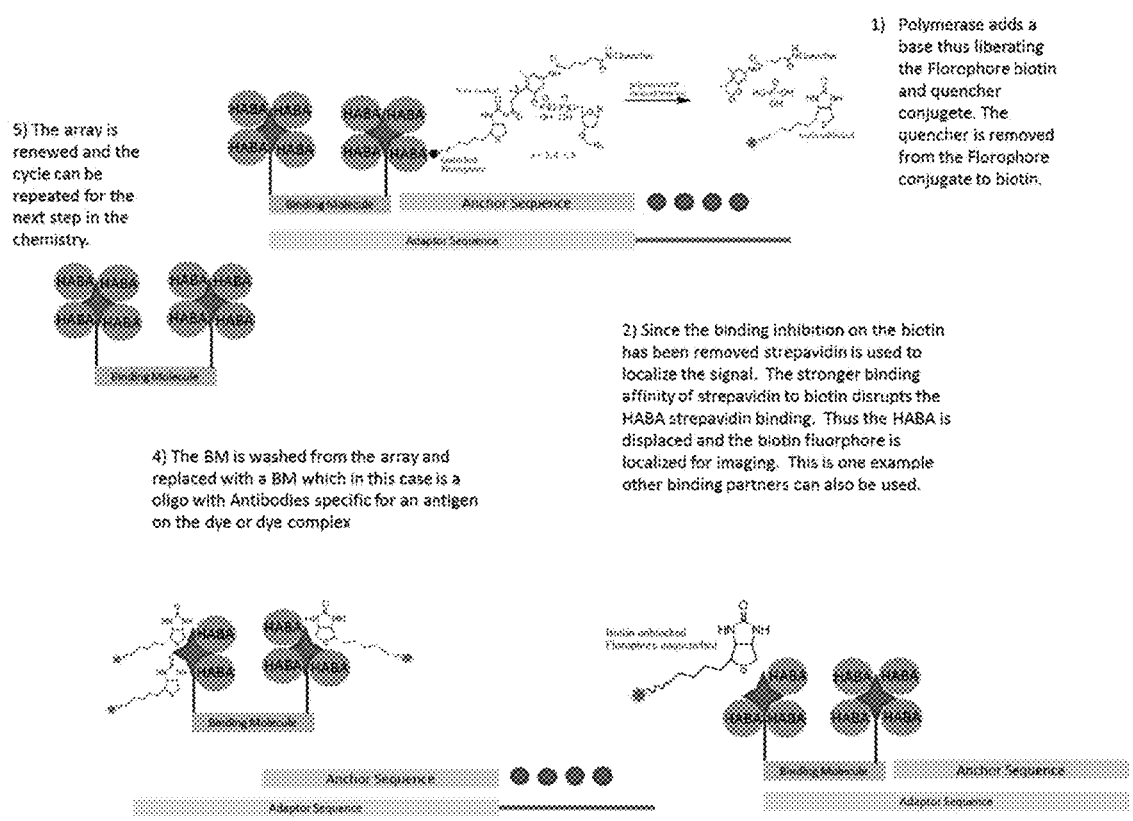
FIGS. 9A and 9B contain sequencing-by-synthesis schemes where the surface capturing is performed through streptavidin-containing capture elements.

FIG. 9A illustrates an embodiment in which the binding moiety of the tag element is blocked so that it cannot bind the corresponding antiligand. In the illustration, the structure blocking the binding moiety comprises a quencher. FIG. 9A also illustrates an embodiment in which the capture element-tag element complex is removed after imaging, rather than only removing the tag element.

In this example, the tag element comprises a fluorophore, biotin, and a quencher. The capture element comprises an oligonucleotide conjugated to streptavidin ("oligonucleotide tethered streptavidin"). The capture element is shown hybridized to an immobilized complementary sequence (adaptor sequence) of a concatemer, but could also be hybrizided to complementary oligonucleotides in other formats. It will be recognized that the complementary sequence on the concatemer is not acting as a "capture element" though it may be structurally similar. Rather, the complementary sequence is analogous to the immobilized complementary oligonucleotide of Illustrative Embodiment 5.

In one embodiment (shown in the figure), the biotin binding sites of streptavidin are occupied by 4'-hydroxyazobenzene-2-carboxylic acid (HABA), a weakly binding analogue of streptavidin.

After base incorporation by the polymerase and cleavage by the phosphatase, the biotin is unblocked and free to bind to a streptavidin capture element, displacing the more weakly binding HABA.

The array is regenerated in two steps. First, the capture element-tag element complex is removed by disrupting the association of the oligonucleotide moiety of the capture element and the complementary sequence to which it binds, and removing (washing away) the capture element-tag element complex. Disruption can be by any suitable method, such as washing the surface with a buffer (optionally with low-salt conditions), washing with hybridization disrupting agents, such as formamide, or heating to melt the oligonucleotide duplex. Second, the capture element is then replaced by adding additional oligonucleotide tethered streptavidin (i.e., a new capture element).

Because the capture element is removed from the array at each cycle, the fluorescent acceptor molecule can be strongly (or non-reversibly) bound to the capture element.

Illustrative Embodiment 9: Regeneration by Removal of the Capture Element

Figure 9B:
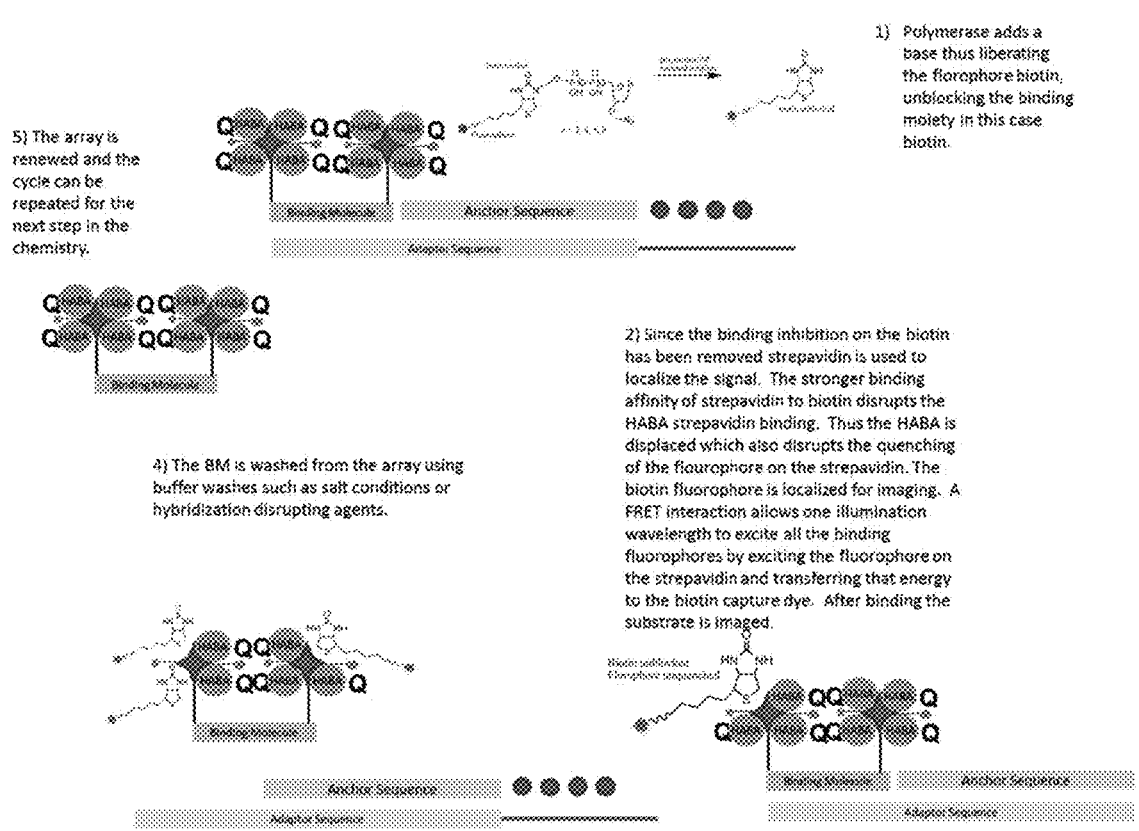

FIG. 9B illustrates a variation of the method of Illustrative Embodiment 8. In this variation, the nucleotide analogue optionally does not include a quencher other than phosphate. Fluorophores are attached to the streptavidin capture elements and corresponding quenchers are attached to the HABA molecules. The HABA quenchers are displaced by the capture of the tag elements. A FRET interaction allows one illumination wavelength to excite all the biotin-conjugated fluorophores by exciting the streptavidin-FRET donor and transferring that energy to the biotin-FRET acceptor fluorophores. Displacement of the HABA allows an appropriate wavelength to be absorbed, which in turn allows detection of the proper base. The sequential addition of single bases allows the presence of a single detection moiety and relieves the requirement for phosphate cleavage.

It will be recognized that there are a variety of variations of the embodiments of this Illustrative Embodiment and Illustrative Embodiment 8. For example, ligand-antiligand combinations other than biotin and streptavidin may be used, capture elements other than oligonucleotides may be used, HABA may be omitted, etc.

Figure 10:
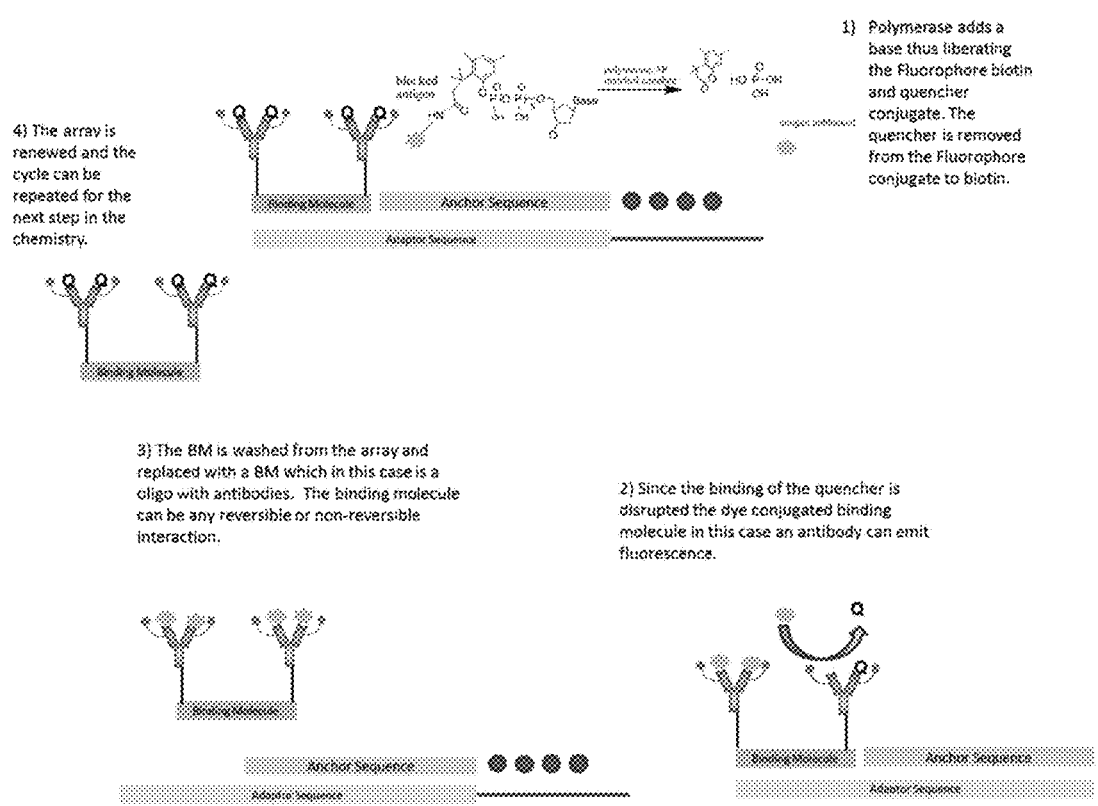
FIG. 10 contains a sequencing-by-synthesis scheme where surface capturing is performed through an inducer in a one-color system.

Illustrative Embodiment 10: A One-Color System in which the Nucleic Acid Analogue does not Comprise (or Optionally Comprises) a Fluorophore Optionally, a one color system can be used, usually requiring the sequential flow of individual bases. In this approach, the nucleotide analogue contains an "inducer" that is released by polymerase cleaving between alpha and beta phosphate and triggering phosphatase, leading to the release of the "inducer." The inducer activates the quenched dye on a capture element. As used in this Illustrative Embodiment, "capture element" refers to a molecule that binds the inducer, and not necessarily a tag element. In FIG. 10, the "capture element" is a complex containing a conjugate of an oligonucleotide tethered monomeric Fab and a fluorophore. As illustrated in FIG. 10, the inducer can be an antigen and the capture element can be an antibody, aptamer, or other binding molecule. The antibody binding site is occupied by a conjugate of a quencher and antigen. After base incorporation by the polymerase and cleavage by the phosphatase, the antigen is unblocked and free to bind a capture element. In this embodiment, the antigen displaces the quencher-antigen complex to bind to the antibody. In the absence of the quencher, the antibody can emit fluorescence for detection.

It will be recognized that in this embodiment, the structure of the nucleotide analogue is

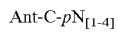

where "Ant" refers to an antigen, C is a cleavable site (e.g., a phosphate bond cleavable by alkaline phosphatase), and pN is as described above.

Examples of suitable antigens for this method include, but are not limited to, biotin, FITC, small molecules such as amino acids, cholesterol, and peptides.

After binding, the substrate is imaged. The array is regenerated and the antigen is released at the completion of the cycle by washing the surface with a buffer (optionally containing a cleavage agent as described herein or with low-pH or low-salt conditions) or with hybridization disrupting agents, such as formamide. Optionally, the array can be regenerated by heating and melting the oligonucleotide.

In some embodiments, a single color sequencing-by-synthesis procedure can be used. For example, different amounts of biotin can be included as an inducer (as further described in Illustrative Embodiment 9) that can vary based on the nucleotide. For example, A can include greater than 99% biotin; T can include approximately 50% biotin; C can include approximately 25% biotin, and G can include less than 10% or no biotin. Since nearly 100% incorporation (e.g., greater than 98%, greater than 99%, or greater than 99.9%) is achieved with the nucleotide analogues described herein in the single extension step and there is no sequence context dependent signal quenching (the dye is not on the incorporated nucleotide), the obtained signals for each base are sufficiently proportional to the fraction of nucleotides with biotin. Using control cycles or multiple real cycles, intensity normalization factors and/or background values can be defined for each DNA spot. Furthermore, intensity or background normalization or correction factors can be defined for each filed image.

Figure 11:
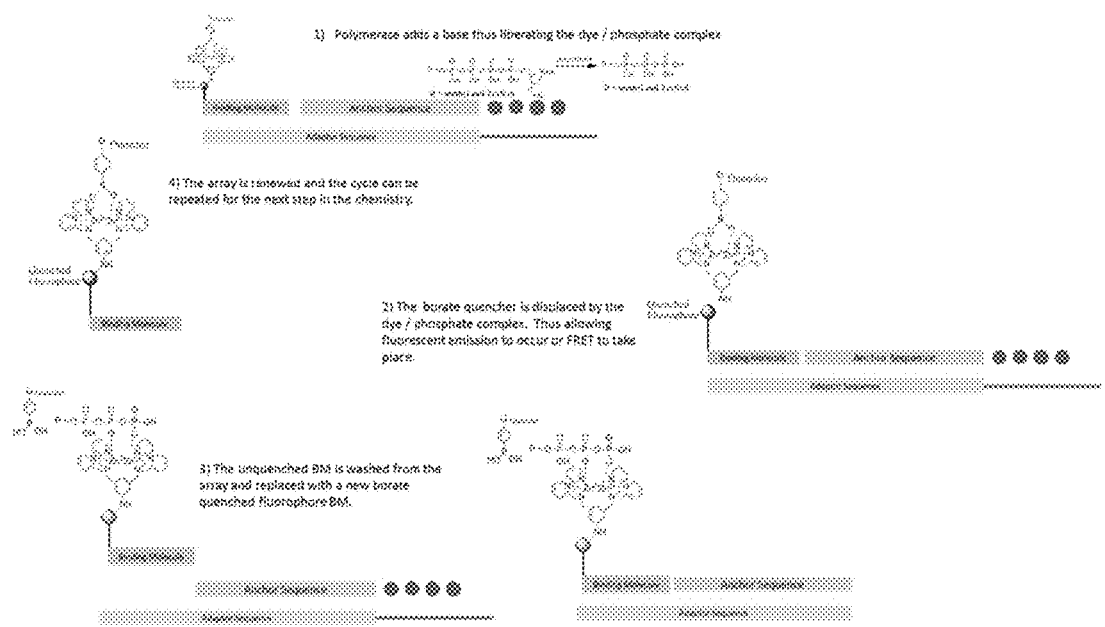
FIG. 11 contains a sequencing-by-synthesis scheme where surface capturing is performed through a borate quencher-containing capture element.

Illustrative Embodiment 11: Surface Capturing Through Borate Quencher-Containing Capture Element FIG. 11 shows a variation in which an oligonucleotide tethered FAM-Zinc-chelate complexed with a quencher-borate conjugate is immobilized near the template. The nucleotide analogue comprises a dye (e.g., methyl or TexRed)-labeled terminal phosphate. A suitable chelator is described by Jang et al., 2005, *J. Org. Chem.* 70:9603-9606

A polymerase incorporates the base and liberates the dye/phosphate complex. The dye/phosphate complex is then captured by tethered FAM-Zinc-chelate, displacing the quencher-borate, to generate an unquenched complex. In the absence of quenching, fluorescent emission (in the case of methyl labels) and/or FRET (in the case of the TexRed label) can occur.

As shown in FIG. 11, the array is regenerated at the completion of the cycle by washing the unquenched capture chelate complex.

Illustrative Embodiment 12: Surface Capturing Through Streptavidin-Containing Capture Elements In the embodiment shown in FIG. 12, the nucleotide analogue contains a blocked biotin as the binding molecule and a quenched FRET pair. The quenched FRET pair has an advantage of low background. The biotin is bound to the terminal phosphaste and thus is blocked from binding to streptavidin. After base incorporation by the polymerase and cleavage by the phosphatase, the biotin is unblocked and free to bind to a capture element (e.g., streptavidin). In addition, the quencher molecule is released so the fluorophore is unquenched.

Figure 12:
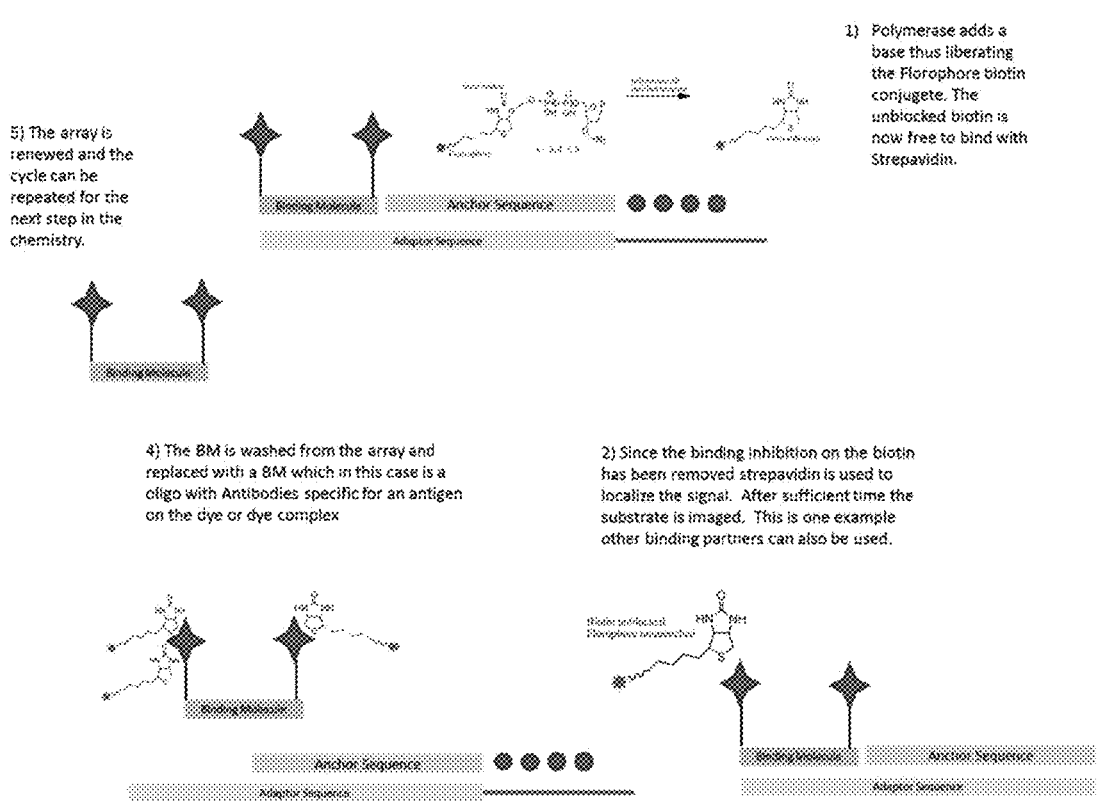
FIG. 12 contains a sequencing-by-synthesis scheme where the surface capturing is performed through streptavidin-containing capture elements.

As shown in the sequencing-by-synthesis embodiment depicted in FIG. 12, the capture element (labeled as "Binding Molecule" in FIG. 12) can be an oligonucleotide with antibodies specific for the tag element. In FIG. 12, the capture element is a conjugate of an oligonucleotide tethered monomeric streptavidin and fluorophore molecules. The nucleotide analogue can provide either a four color or two color system for the method. Specifically, due to the use of the same capture element, there is no bias in the affinity of the ligand and anti-ligand binding for different dyes. Since all molecules are captured at relatively similar rates, proportions of labeled molecules can be discerned in a mixture. Thus, high affinity binding limits diffusion, thus enabling detection of the dye proportions in a two color system.

Streptavidin localizes the signal. After sufficient time, the substrate is imaged. The array is regenerated at the completion of the cycle by washing the surface with a buffer (optionally with low-salt conditions) or with hybridization disrupting agents, such as formamide. Optionally, the array can be regenerated by heating and melting the oligonucleotide. The capture element is then replaced.

Figure 13:
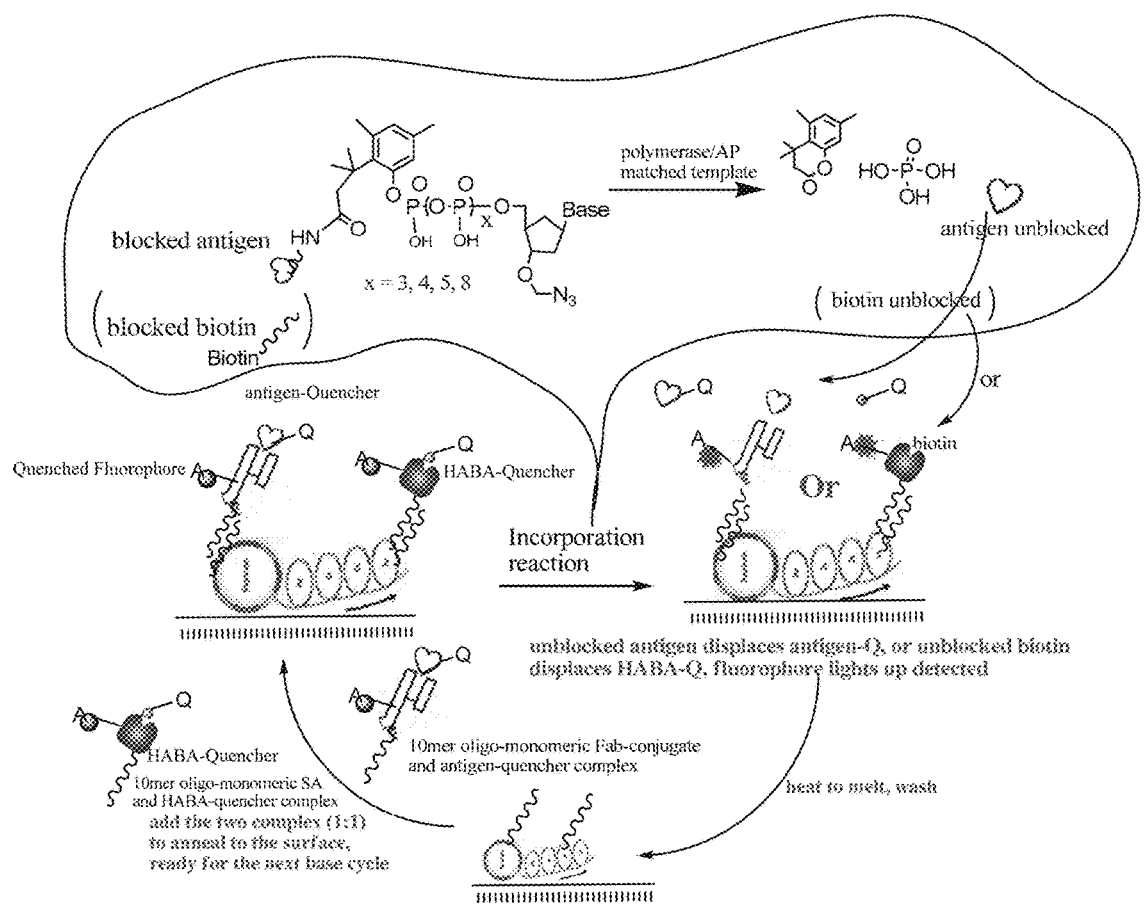
FIG. 13 contains a sequencing-by-synthesis scheme where surface capturing is performed through an inducer in a two-color system.

Illustrative Embodiment 13 Surface Capturing Through Inducer in a Two-Color System As shown in the sequencing-by-synthesis embodiment depicted in FIG. 13, two different capture elements can be used. The first capture element can be a complex between the conjugate of an oligonucleotide-tethered monomeric Fab and fluorophore molecules and the conjugate of an antigen-fluorescent quencher molecule. The second capture element can be a complex between the conjugate of an oligonucleotide tethered monomeric streptavidin and fluorophore molecules and the conjugate of a HABA-fluorescent quencher molecule.

The nucleotide analogue contains a blocked inducer, such as biotin or an antigen epitope. After base incorporation by the polymerase and cleavage by the phosphatase, the antigen or biotin is unblocked and free to bind a capture element. The unblocked antigen can then displace the antigen-quencher molecule. The unblocked biotin can displace the HABA-quencher molecule. In this method, the antigen can be associated with one dye and biotin can be associated with a different dye. In turn, the fluorophore is no longer quenched and can be detected. Examples of the antigens Include, for example, biotin, FITC, small molecules such as amino adds, cholesterol, and peptides.

After binding, the substrate is imaged. The array is regenerated at the completion of the cycle by washing the surface with a buffer (optionally with low-salt conditions) or with hybridization disrupting agents, such as formamide. Optionally, the array can be regenerated by heating and melting the oligonucleotide. The capture element is then replaced.

The compounds and methods of the appended claims are not limited in scope by the specific compounds and methods described herein, which are intended as illustrations of a few aspects of the claims and any compounds and methods that are functionally equivalent are within the scope of this disclosure. Various modifications of the compounds and methods in addition to those shown and described herein are intended to fall within the scope of the appended claims. Further, while only certain representative compounds, methods, and aspects of these compounds and methods are specifically described, other compounds and methods and combinations of various features of the compounds and methods are intended to fall within the scope of the appended claims, even if not specifically recited. Thus, a combination of steps, elements, components, or constituents may be explicitly mentioned herein; however, all other combinations of steps, elements, components, and constituents are included, even though not explicitly stated. All publications, patents, and patent applications cited herein are hereby incorporated by reference in their entireties for all purposes.

What is claimed is:

1. A method for sequencing a target nucleic acid, comprising:
   a) providing a template nucleic acid immobilized on a surface, a primer, a polymerase, and a nucleotide analogue of the following structure:

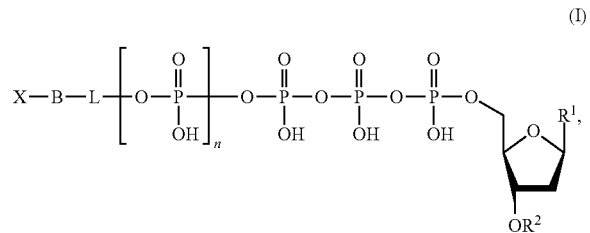

wherein
   n is 0, 1, 2, 3, 4, 5, 6, or 7;
   L is absent or a linking group;
   $R^1$ is a nucleoside base;
   $R^2$ is hydrogen or a blocking group;
   B is a binding molecule; and
   X is a detection label, wherein said detection label is quenched;
   b) extending the primer by incorporating the nucleotide analogue;
   c) providing a phosphatase to cleave between the binding molecule and the linking group or between the binding molecule and the terminal phosphate, thereby generating a fragment of (I) comprising the label and the binding molecule, wherein the label is unquenched;
   d) binding the fragment to a capture element immobilized on a surface; and
   e) detecting a fluorescence emission from the label of the fragment captured on the surface.

2. The method of claim 1, wherein the binding molecule comprises an oligonucleotide.

3. The method of claim 1, wherein the capture element comprises a thio or thiol containing molecule.

4. The method of claim 1, wherein the capture element comprises streptavidin, an antibody, a protein, or a dendrimer.

5. The method of claim 1, wherein the capture element comprises an oligonucleotide immobilized complementary to the template nucleic acid.

6. The method of claim 1, wherein the template nucleic acid is an immobilized DNA concatemer comprising multiple copies of an adaptor sequence.

7. The method of claim 1, wherein L is a linking group and the linking group further comprises a quencher.

8. The method of claim 7, wherein the providing step comprises displacing the quencher from the linking group.

9. The method of claim 1, further comprising removing the fragment from the capture element on the surface.

10. The method of claim 9, wherein the removing step comprises heating the fragment and the capture element.

11. The method of claim 9, wherein the removing step comprises washing the fragment and the capture element with a buffer.

12. The method of claim 9, wherein the removing step comprises adding an enzyme to cleave the fragment from the capture element.

13. The method of claim 1, further comprising cleaving the blocking group from the incorporated nucleotide analogue.

14. The method of claim 1, wherein the detecting step is performed using fluorescence resonance energy transfer.

15. The method of claim 1, wherein L is absent.

16. The method of claim 1, wherein L is a linking group and the linking group is a substituted or unsubstituted alkyl, substituted or unsubstituted alkenyl, or substituted or unsubstituted aryl.

17. The method of claim 16, wherein the linking group is a methylene group or a phenyl group.

18. The method of claim 1, wherein the binding molecule and capture element are a binding pair selected from biotin-streptavidin, biotin-avidin, antibody-antigen, and a complementary oligonucleotide pair capable of forming a nucleic acid duplexes.

19. The method of claim 1, wherein the blocking group is an amino-containing compound, an allyl-containing compound, an azido-containing compound, an alkoxy-containing compound, polyethylene glycol, or a substituted or unsubstituted alkyl.

20. The method of claim 1, wherein the blocking group is $NH_2$, $-CH_2CH=CH_2$, $-CH_2N_3$, $-CH_2OCH_3$, or polyethylene glycol.

* * * * *